United States Patent [19]
Donovan et al.

[11] Patent Number: 5,962,264
[45] Date of Patent: Oct. 5, 1999

[54] **METHOD OF REDUCING THE PROTEOLYTIC DEGRADATION OF *BACILLUS THURINGIENSIS* INSECTICIDAL TOXIC PROTEIN**

[75] Inventors: William P. Donovan, Levittown, Pa.; Yuping Tan, Menlo Park, Calif.

[73] Assignee: Monsanto Company, St. Louis, Mo.

[21] Appl. No.: 09/086,662

[22] Filed: May 29, 1998

Related U.S. Application Data

[62] Division of application No. 08/415,823, Mar. 31, 1995, Pat. No. 5,759,538.

[51] Int. Cl.$^6$ .................................................. C12P 21/06
[52] U.S. Cl. .................... 435/69.1; 435/212; 435/219; 435/252.31; 435/320.1; 536/23.2
[58] Field of Search .................................... 435/212, 219, 435/69.1, 320.1, 471, 23.2, 252.31, 220; 536/23.7, 23.71; 530/350, 300

[56] References Cited

U.S. PATENT DOCUMENTS

| | | | |
|---|---|---|---|
| 4,695,455 | 9/1987 | Barnes et al. | 424/93 |
| 4,695,462 | 9/1987 | Barnes et al. | 424/195.1 |
| 4,766,077 | 8/1988 | Orser et al. | 435/253 |
| 4,828,994 | 5/1989 | Fahnestock et al. | 435/172.3 |
| 4,935,353 | 6/1990 | Burges et al. | 435/69.1 |
| 5,073,632 | 12/1991 | Donovan | 536/27 |
| 5,080,897 | 1/1992 | Gonzalez, Jr. et al. | 424/93 |
| 5,264,364 | 11/1993 | Donovan et al. | 435/252.5 |
| 5,304,484 | 4/1994 | Delecluse et al. | 435/252.31 |
| 5,322,687 | 6/1994 | Donovan et al. | 424/93 A |

FOREIGN PATENT DOCUMENTS

| | | |
|---|---|---|
| 0 339 009 - A2 | 10/1989 | European Pat. Off. . |
| A-4278092 | 10/1992 | Japan . |
| WO92/14826 | 9/1992 | WIPO . |
| WO 94/24264 | 10/1994 | WIPO . |

OTHER PUBLICATIONS

Tan & Donovan, "Cloning and Characterization of the Alkaline Protease Gene of *Bacillus thuringiensis*," Abstract of the 95th General Meeting of the American Society for Microbiology, Washington, DC, 95:406 (May 1995).

M. Bhattacharya et al., "Nonenzymatic Glycosylation of Lepidopteran–Active *Bacillus thuringiensis* Protein Crystals," *Applied and Environmental Microbiology*, 59(8):2666–2672 (Aug. 1993).

H.P. Bietlot et al., "Evidence That the CryIA Crystal Protein from *Bacillus thuringiensis* is Associated with DNA," *The Journal of Biological Chemistry*, 268(11):8240–8245 (Apr. 1993).

C. Chang et al., "High–Level cryIVD and cytA Gene Expression in *Bacillus thuringiensis* Does Not Require the 20–Kilodalton Protein, and the Coexpressed Gene Products are Synergistic in Their Toxicity to Mosquitoes," *Applied and Environmental Microbiology*, 59(3): 815–821 (Mar. 1993).

C.C. Beegle et al., "Invitation Paper (C.P. Alexander Fund): History of *Bacillus thuringiensis* Berliner Research and Development," *The Canadian Entomologist*, 124:587–616 (Jul./Aug. 1992).

B.E. Tabashnik, "Evaluation of Synergism among *Bacillus thuringiensis* Toxins," *Applied and Environmental Microbiology*, 58(10):3343–3346 (Oct. 1992).

X. Yan et al., "Chemical Modification of *Bacillus thuringiensis* subsp. *thuringiensis* (HD–524) Trypsin–Activated Endotoxin: Implication of Tyrosine Residues in Lepidopteran Cell Lysis," *Journal of Invertebrate Pathology*, 57:101–108 (1991).

A. Delécluse et al., "Deletion by In Vivo Recombination Shows that the 28–Kilodalton Cytolytic Polypeptide from *Bacillus thuringiensis* subsp. *israelensis* Is Not Essential for Mosquitocidal Activity," *Journal of Bacteriology*, 173(11):3374–3381 (Jun. 1991).

C.N. Chilcott et al., "Comparative Toxicity of *Bacillus thuringiensis* var. *israelensis* Crystal Proteins in vivo and in vitro," *Journal of General Microbiology*, 134:2551–2558 (1988).

W.P. Donovan et al., "Polynucleotide phosphorylase and ribonuclease II are required for cell viability and mRNA turnover in *Escherichia coli* K–12," *Proc. Natl. Acad. Sci. USA*, 83:120–124 (Jan. 1986).

S–L. Wong et al., "The subtilisin E gene of *Bacillus subtilis* is transcribed from a $\sigma^{37}$ promoter in vivo," *Proc. Natl. Acad. Sci. USA*, 81:1184–1188 (Feb. 1984).

D. Perlman et al., "A Putative Signal Peptidase Recognition Site and Sequence in Eukaryotic and Prokaryotic Signal Peptides," *J. Mol. Biol.*, 167:391–409 (1983).

W.P. Donovan et al., "Amplification of ribonuclease II (rnb) activity in *Escherichia coli* K–12," *Nucleic Acids Research*, 11(2):265–275 (1983).

T. Kivity–Vogel et al., "On the Metabolic Inactivation of Messenger RNA in *Escherichia coli:* Ribonuclease I and Polynucleotide Phosphorylase," *Biochim. Biophys. Acta*, 138:66–75 (1967).

(List continued on next page.)

*Primary Examiner*—Robert A. Wax
*Assistant Examiner*—Nashaat T. Nashed
*Attorney, Agent, or Firm*—Panitch Schwarze Jacobs & Nadel, P.C.

[57] ABSTRACT

The present invention is based on the discovery, isolation, sequencing and characterization of two protease genes present in B.t. One is an alkaline protease gene generally designated "apr." The other is a neutral protease gene generally designated "npr." The invention also includes genetically disabling the apr and the npr genes to reduce proteolytic activity of the proteases encoded by the genes, and using the disabled genes in insecticidal B.t. constructs along with one or more B.t. protein toxin genes. These resulting B.t. constructs are useful for the enhanced production of B.t. toxin protein. The B.t. toxin protein recovered from the fermentation production of these B.t. constructs also exhibits improved stability with respect to its insecticidal activity.

15 Claims, 11 Drawing Sheets

OTHER PUBLICATIONS

A.G. O'Donnell et al., "An Investigation of the Relationship between *Bacillus cereus, Bacillus thuringiensis* and *Bacillus mycoides* using Pyrolysis Gas–Liquid Chromatography," *Journal of General Microbiology*, 119:189–194 (1980).

R. Har–El et al., "Synthesis and Degradation of lac mRNA in *E. coli* Depleted of 30S Ribosomal Subunits," *Molec. Gen. Genet.*, 173:135–144 (1979).

R.V. Krishna et al., "Polynucleotide Phosphorylase Has a Role in Growth of *Escherichia coli*," *Journal of Bacteriology*, 113:1235–1239 (1973).

H.J. Somerville et al., "DNA Competition Studies within the *Bacillus cereus* Group of Bacilli," *Journal of General Microbiology*, 73:257–265 (1972).

E.T. Lennette et al., "An *Escherichia coli* Mutant with Increased Messenger Ribonuclease Activity," *Proc. Nat. Acad. Sci. USA*, 68(12):3140–3144 (1971).

M.H. Rogoff et al., "*Bacillus Thuringiensis:* Microbiological Considerations," *Annual Review of Microbiology*, C.E. Clifton et al., eds, Palo Alto, Calif., 23:357–385 (1969).

T. Kivity–Vogel et al., "A Correlation Between Ribonuclease II and the In Vivo Inactivation of Messenger RNA in *E. Coli*," *Biochem. Biophys. Res. Comm.* 35:412–417 (1968).

P.F. Spahr, "Purification and Properties of Ribonuclease II from *Escherichia coli*," *The Journal of Biological Chemistry*, 239(11):3716–3726 (Nov. 1964).

M. Grunberg–Manago, "Polynucleotide Phosphorylase," *Prog. in Nucleic Acid Res.*, J.N. Davidson & Cohn, W.F., eds, 1:93–133 (1963).

Maria Y. Yang et al., "Cloning of the Neutral Protease Gene of *Bacillus subtilis* and the Use of the Cloned Gene to Create an In Vitro–Derived Deletion Mutation," *Journal of Bacteriology*, 160(1), pp. 15–21 (Oct. 1984).

P. Thurley et al., "Characterization of Proteolytic Activity Associated With *Bacillus thuringiensis* var. *darmstadiensis* Crystals," *FEMS Microbiology Letters*, 27, pp. 221–225 (1985).

Valentin M. Stepanov et al., "A New Subfamily of Microbial Serine Proteinases ? Structural Similarities of *Bacillus thuringiensis* and *Thermoactinomyces vulgaris* Extracellular Serine Proteinases," *Biochemical and Biophysical Research Communications*, 100(4), pp. 1680–1687 (Jun. 1981).

Mark L. Stahl et al., "Replacement of the *Bacillus subtilis* Subtilisin Structural Gene with an In Vitro–Derived Deletion Mutation," *Journal of Bacteriology*, 158(2), pp. 411–418 (May 1984).

Walter Sidler et al., "The Primary Structure of *Bacillus cereus* Neutral Proteinase and Comparison with Thermolysin and *Bacillus subtilis* Neutral Proteinase," 367, pp. 643–657 (Jul. 1986).

Gautam Sarath et al., "Protease Assay Methods," Proteolytic Enzymes—A Practical Approach, IRL Press, Eynsham, Oxford, England, pp. 25–31 & 55, (1989, 1990)—Edited by R.J. Beynon, Department of Biochemistry, University of Liverpool, UK and J.S. Bond, Department of Biochemistry, Virginia Polytechnic Institute and State University, Blacksburg, VA, USA.

M. Pozsgay et al., "The Effect of Sunlight on the Protein Crystals from *Bacillus thuringiensis* var. *kurstaki* HD1 and NRD12: A Raman Spectroscopic Study," *Journal of Invertebrate Pathology,* 50, pp. 246–253 (1987).

Mary Ann Pfannenstiel et al., "Toxicity and Composition of Protease–Inhibited *Bacillus thuringiensis* var. *israelensis* Crystals," *FEMS Microbiology Letters,* 21, pp. 39–42 (1984).

D. Pearson et al., "Bioinsecticide Activity, Bacterial Cell Lysis and Proteolytic Activity in Cultures of *Bacillus thuringiensis* subsp. *israelensis," Journal of Applied Bacteriology,* 65, pp. 195–202 (1988).

Nancy Bedient Norton et al., "Construction and Characterization of Plasmid Vectors for Cloning in the Entomocidal Organism *Bacillus sphaericus* 1593," *Plasmid,* 13, pp. 211–214 (1985).

Bedrich Meloun et al., "Complete Primary Structure of Thermitase from *Thermoactinomyces vulgaris* and Its Structural Features Related to the Subtilisin–type Proteinases," *FEBS,* 183(2), pp. 195–200 (Apr. 1985).

O.N. Morris, "Protection of *Bacillus thuringiensis* from Inactivation by Sunlight," *The Canadian Entomologist,* 115, pp. 1215–1227 (Sep. 1983).

A. Lövgren et al., "Molecular Characterization of Immune Inhibitor A, a Secreted Virulence Protease from *Bacillus thuringiensis," Molecular Microbiology,* 4(12), pp. 2137–2146 (1990).

Anthony Macaluso et al., "Efficient Transformation of *Bacillus thuringiensis* Requires Nonmethylated Plasmid DNA," *Journal of Bacteriology,* 173(3), pp. 1353–1356 (Feb. 1991).

Eugenia Li et al., "Metalloprotease from *Bacillus thuringiensis," Applied Microbiology,* 30(3), pp. 354–361 (Sep. 1975).

Marguerite–M. Lecadet et al., "Characterization of an Intracellular Protease Isolated from *Bacillus thuringiensis* Sporulating Cells and Able to Modify Homologous RNA Polymerase," *Eur. J. Biochem.,* 79, pp. 329–338 (1977).

Akane Kunitate et al., "Purification and Characterization of a Thermostable Serine Protease from *Bacillus thuringiensis," Agric. Biol. Chem.,* 53(12), pp. 3251–3256 (1989).

Herman Höfte et al., "Insecticidal Crystal Proteins of *Bacillus thuringiensis," Microbiological Reviews,* 53(2), pp. 242–255 (Jun. 1989).

C.N. Chilcott et al., "Characterization of Proteolytic Activity Associated with *Bacillus thuringiensis* var. *israelensis* Crystals," *FEMS Microbiology Letters,* 18, pp. 37–41, (1983).

G.G. Chestukhina et al., "Proteinases Bound to Crystals of *Bac. thuringiensis," Biochem.,* 43, pp. 681–686 (1978).

Lee A. Bulla, Jr. et al., "Characterization of the Entomocidal Parasporal Crystal of *Bacillus thuringiensis," Journal of Bacteriology,* 130(1), pp. 375–383 (Apr. 1977).

Margaret Bibilos et al., "Inhibition of *Bacillus thuringiensis* Proteases and Their Effects on Crystal Toxin Proteins and Cell–Free Translations," *Can. J. Microbiol.,* 34, pp. 740–747 (1988).

Wetmore et al., "The role of the pro–sequence in the processing and secretion of the thermolysin–like neutral protease from *Bacillus cereus"* Mol. Microbiol. 6(12), 1593–1604.

W.P. Donovan et al., "Cloning of the nprA Gene for Neutral Protease A of *Bacillus thuringiensis* and Effect of In Vivo Deletion of nprA on Insecticidal Crystal Protein," Applied and Environmental Microbiology, 63(6):2311–2317 (Jun. 1997).

FIGURE 1A

```
         10         20         30         40         50         60
AAAAGGAATGACTCATACATGATGAGCGTTCCTTTTTTCATCCCCTCTTTTACTTAATTA 70         80         90        100        110        120
CTATCATTAAAAATATATTTATATCAATATTTACTCCTTTTTATTCCTTCAAAAGTTTTT 130        140        150        160        170        180
CACATAAATGTCATAAATCGTATGGTTTAACTATATAGTTGAAAAGGAATGCGACATTAA 190        200        210        220        230        240
GGTGTCACTGAAAAACTCATCCAAGAAAAGGGAGGAAAAATCTTTTGAAAAACAAAATCA
                                              MetLysAsnLysIleI 250        260        270        280        290        300
TCGTTTTCCTATCTGTTTTGTCATTTATTATTGGTGGTTTCTTCTTTAACACGAATACTT
leValPheLeuSerValLeuSerPheIleIleGlyGlyPhePhePheAsnThrAsnThrS 310        320        330        340        350        360
CAAGCGCTGAAACATCATCTACTGATTACGTTCCTAACCAATTAATCGTTAAGTTCAAAC
erSerAlaGluThrSerSerThrAspTyrValProAsnGlnLeuIleValLysPheLysG 370        380        390        400        410        420
AAAATGCATCTTTAAGTAATGTGCAATCTTTTCATAAATCTGTCGGAGCTAATGTCTTAT
lnAsnAlaSerLeuSerAsnValGlnSerPheHisLysSerValGlyAlaAsnValLeuS 430        440        450        460        470        480
CTAAAGATGATAAGTTAGGTTTTGAAGTCGTACAATTTTCAAAAGGTACTGTAAAAGAAA
erLysAspAspLysLeuGlyPheGluValValGlnPheSerLysGlyThrValLysGluL 490        500        510        520        530        540
AAATAAAGAGCTATAAAAATAATCCAGATGTGGAATATGCAGAACCGAATTATTACGTTC
ysIleLysSerTyrLysAsnAsnProAspValGluTyrAlaGluProAsnTyrTyrValH 550        560        570        580        590        600
ACGCCTTTTGGACTCCAAACGACCCATATTTTAATAATCAATACGGGTTACAAAAGATTC
isAlaPheTrpThrProAsnAspProTyrPheAsnAsnGlnTyrGlyLeuGlnLysIleG 610        620        630        640        650        660
AAGCTCCACAAGCTTGGGATAGCCAACGAAGTGATCCTGGTGTAAAAGTAGCTATTATTG
lnAlaProGlnAlaTrpAspSerGlnArgSerAspProGlyValLysValAlaIleIleA 670        680        690        700        710        720
ATACAGGAGTTCAAGGCTCACACCCTGATCTGGCTTCGAAAGTAATTTACGGGCATGATT
spThrGlyValGlnGlySerHisProAspLeuAlaSerLysValIleTyrGlyHisAspT 730        740        750        760        770        780
ATGTTGATAACGACAATACATCTGATGATGGTAATGGTCATGGTACACATTGCGCTGGAA
yrValAspAsnAspAsnThrSerAspAspGlyAsnGlyHisGlyThrHisCysAlaGlyI 790        800        810        820        830        840
TTACTGGAGCACTTACGAATAACAGCGTCGGAATTGCTGGTGTTGCCCCACAAACTTCAA
leThrGlyAlaLeuThrAsnAsnSerValGlyIleAlaGlyValAlaProGlnThrSerI
```

FIGURE 1B

```
         850       860       870       880       890       900
TTTATGCTGTCCGCGTATTAGATAATCAAGGAAGTGGTACTCTTGATGCTGTAGCGCAAG
 leTyrAlaValArgValLeuAspAsnGlnGlySerGlyThrLeuAspAlaValAlaGlnG 910       920       930       940       950  SstI  960
GTATTCGAGAAGCTGCTGATTCGGGTGCAAAAGTAATTAGTTTAAGTTTAGGAGCTCCAA
 lyIleArgGluAlaAlaAspSerGlyAlaLysValIleSerLeuSerLeuGlyAlaProA 970       980       990      1000      1010      1020
ATGGTGGTACTGCATTACAACAAGCCGTTCAATATGCATGGAATAAAGGCTCTGTTATAG
 snGlyGlyThrAlaLeuGlnGlnAlaValGlnTyrAlaTrpAsnLysGlySerValIleV 1030      1040      1050      1060      1070      1080
TTGCAGCTGCTGGAAATGCTGGAAATACAAAAGCTAATTACCCTGCTTATTACAGCGAAG
 alAlaAlaAlaGlyAsnAlaGlyAsnThrLysAlaAsnTyrProAlaTyrTyrSerGluV 1090      1100      1110      1120      1130      1140
TAATTGCAGTTGCTTCTACAGATCAATCAGATAGAAAATCTTCATTCTCTACTTATGGTA
 alIleAlaValAlaSerThrAspGlnSerAspArgLysSerSerPheSerThrTyrGlyS 1150      1160      1170      1180      1190      1200
GCTGGGTAGATGTTGCAGCACCAGGTTCAAATATATATTCAACATATAAAGGAAGCACGT
 erTrpValAspValAlaAlaProGlySerAsnIleTyrSerThrTyrLysGlySerThrT 1210      1220      1230      1240      1250      1260
ATCAATCATTAAGTGGTACATCTATGGCAACACCTCATGTTGCAGGAGTCGCAGCTCTTT
 yrGlnSerLeuSerGlyThrSerMetAlaThrProHisValAlaGlyValAlaAlaLeuL 1270      1280      1290      1300      1310      1320
TAGCAAATCAAGGATATAGCAATACACAAATCCGCCAAATTATTGAGTCTACTACTGATA
 euAlaAsnGlnGlyTyrSerAsnThrGlnIleArgGlnIleIleGluSerThrThrAspL 1330      1340      1350      1360      1370      1380
AAATTAGTGGTACAGGTACGTACTGGAAAAACGGTAGAGTCAATGCATATAAGGCTGTAC
 ysIleSerGlyThrGlyThrTyrTrpLysAsnGlyArgValAsnAlaTyrLysAlaValG 1390      1400      1410      1420      1430      1440
AATACGCTAAGCAATTACAAGAAAATAAAGCTTCTTAAGAAAACTTTAATCAGTCGATCT
 lnTyrAlaLysGlnLeuGlnGluAsnLysAlaSerEnd 1450      1460      1470      1480      1490      1500
ACCATGAATGCAGAATAAAATAGAAGGAGAGACTTCTATAATTAAAGCCTCTCCTTCTTA 1510      1520      1530      1540      1550      1560
CAAACTATATTACTCTCCCTGCTTTTTAACCATATGTAAATACAGTACAAAATCCATCAT 1570      1580      1590      1600      1610      1620
TGTCGATGAATGACCAAGTTGACGAATCATCGCTGTTATATTTCCTCTATGATATGTACC 1630      1640      1650      1660      1670      1680
ATGATTTACGACATGTTGCACTAATTCTAAAATCGAAGTTTCTAATTTCCCTACGTATGG 1690      1700      1710      1720      1730      1740
ATTCTCAATAACAAATACAGCATTCACATCTTGTATTGTAATTAAAAACTCTTTATATTG

1750
ATTTGCCATG
```

FIGURE 2A

```
         10        20        30        40        50        60
TAAGAAAATATTGAAAAAACCCCTTTCCAATCGGAAAGGGGTTTTTTCAATATTTGTTCC 70        80        90       100       110       120
TCAAAATTCTACAAAACTTGAGAAATAAATTAATTGAATTTTTAGTATATTAATAGTGGA 130       140       150       160       170       180
AACATAATGCTAATATGAAACTACTCTTTTTCAAAAAATTTTTTATTAGGGGGAAGGTTA 190       200       210       220       230       240
TATGAAAAAGAAGAGTTTAGCATTAGTGTTAGCGACAGGAATGGCAGTTACAACGTTTGG
 MetLysLysLysSerLeuAlaLeuValLeuAlaThrGlyMetAlaValThrThrPheGl 250       260       270       280       290       300
AGGGACAGGCTCTGCGTTTGCGGATTCTAAAAATGTGCTCTCTACTAAGAAGTACAATGA
yGlyThrGlySerAlaPheAlaAspSerLysAsnValLeuSerThrLysLysTyrAsnGl 310       320       330       340       350       360
GACGGTGCAGTCACCTGAGTTTATTTCTGGTGATCTAACTGAAGCAACTGGCAAGAAAGC
uThrValGlnSerProGluPheIleSerGlyAspLeuThrGluAlaThrGlyLysLysAl 370       380       390       400       410       420
AGAATCTGTTGTGTTTGATTACTTAAACGCAGCAAAAGGTGATTACAAGCTAGGGGAAAA
aGluSerValValPheAspTyrLeuAsnAlaAlaLysGlyAspTyrLysLeuGlyGluLy 430       440       450       460       470       480
GAGTGCACAAGATTCTTTCAAAGTGAAACAAGTGAAGAAAGATGCTGTAACTGATTCAAC
sSerAlaGlnAspSerPheLysValLysGlnValLysLysAspAlaValThrAspSerTh 490       500       510       520       530       540
AGTAGTACGTATGCAACAAGTTTACGAAGGAGTGCCTGTATGGGGTTCTACTCAAGTAGC
rValValArgMetGlnGlnValTyrGluGlyValProValTrpGlySerThrGlnValAl 550       560       570       580       590       600
TCACGTAAGTAAGGACGGTTCTTTAAAAGTATTGTCTGGAACAGTTGCACCTGATTTAGA
aHisValSerLysAspGlySerLeuLysValLeuSerGlyThrValAlaProAspLeuAs 610       620       630       640       650       660
CAAAAAGGAAAAGTTGAAAAATAAAAATAAGATTGAAGGCGCAAAAGCAATTGAAATCGC
pLysLysGluLysLeuLysAsnLysAsnLysIleGluGlyAlaLysAlaIleGluIleAl 670       680       690       700       710       720
GCAGCAAGATTTAGGGGTAACACCGAAATATGAAGTAGAACCAAAAGCGGACTTATATGT
aGlnGlnAspLeuGlyValThrProLysTyrGluValGluProLysAlaAspLeuTyrVa 730       740    NdeI750NdeI  760       770       780
ATATCAAAACGGTGAGGAAACAACATATGCATATGTTGTAAATCTAAACTTCTTAGATCC
lTyrGlnAsnGlyGluGluThrThrTyrAlaTyrValValAsnLeuAsnPheLeuAspPr 790       800       810       820       830       840
AAGCCCAGGAAACTACTACTATTTCATTGAGGCAGACAGCGGTAAAGTATTAAATAAGTT
oSerProGlyAsnTyrTyrTyrPheIleGluAlaAspSerGlyLysValLeuAsnLysPh
```

FIGURE 2B

```
       850        860        870        880        890        900
TAATACAATTGATCATGTGACGAATGATGATAAGTCACCAGTTAAGCAAGAGGCTCCTAA
eAsnThrIleAspHisValThrAsnAspAspLysSerProValLysGlnGluAlaProLy 910        920        930        940        950        960
ACAGGATGCGAAAGCTGTTGTAAAGCCTGTAACAGGAACGAATAAAGTAGGAACTGGTAA
sGlnAspAlaLysAlaValValLysProValThrGlyThrAsnLysValGlyThrGlyLy 970        980        990       1000       1010       1020
AGGCGTACTAGGAGATACGAAGTCTCTTAATACAACGTTATCTGGATCATCTTACTACTT
sGlyValLeuGlyAspThrLysSerLeuAsnThrThrLeuSerGlySerSerTyrTyrLe 1030       1040       1050   NdeI1060       1070       1080
ACAAGATAATACACGCGGGGCAACGATTTTCACATATGATGCGAAAAACCGTTCAACATT
uGlnAspAsnThrArgGlyAlaThrIlePheThrTyrAspAlaLysAsnArgSerThrLe 1090       1100       1110       1120       1130       1140
ACCAGGAACATTATGGGCAGATGCAGATAATGTTTTCAATGCAGCGTATGATGCAGCAGC
uProGlyThrLeuTrpAlaAspAlaAspAsnValPheAsnAlaAlaTyrAspAlaAlaAl 1150       1160       1170       1180       1190       1200
GGTAGATGCTCATTACTATGCGGGTATCACGTATGATTACTATAAGAATACATTTAATCG
aValAspAlaHisTyrTyrAlaGlyIleThrTyrAspTyrTyrLysAsnThrPheAsnAr 1210       1220       1230       1240       1250       1260
TAATTCAATTAATGATGCAGGAGCGCCGTTAAAATCAACAGTTCATTACGGAAGTAATTA
gAsnSerIleAsnAspAlaGlyAlaProLeuLysSerThrValHisTyrGlySerAsnTy 1270       1280       1290       1300       1310       1320
TAACAATGCATTCTGGAACGGATCACAGATGGTATACGGAGATGGTGATGGTGTAACATT
rAsnAsnAlaPheTrpAsnGlySerGlnMetValTyrGlyAspGlyAspGlyValThrPh 1330       1340       1350       1360       1370       1380
TACTTCATTATCTGGTGGAATTGATGTAATTGGTCACGAGTTAACGCATGCTGTTACGGA
eThrSerLeuSerGlyGlyIleAspValIleGlyHisGluLeuThrHisAlaValThrGl 1390       1400       1410       1420       1430       1440
AAATAGTTCAAATCTAATTTATCAAAATGAATCAGGGGCTTTAAATGAAGCGATTTCTGA
uAsnSerSerAsnLeuIleTyrGlnAsnGluSerGlyAlaLeuAsnGluAlaIleSerAs 1450       1460       1470       1480       1490       1500
TATCTTTGGTACTTTAGTAGAATTCTATGATAACCGTAACCCGGATTGGGAGATTGGTGA
pIlePheGlyThrLeuValGluPheTyrAspAsnArgAsnProAspTrpGluIleGlyGl 1510       1520       1530       1540       1550       1560
AGATATTTACACACCTGGTAAAGCAGGAGACGCGCTTCGCTCTATGAGTGATCCTACGAA
uAspIleTyrThrProGlyLysAlaGlyAspAlaLeuArgSerMetSerAspProThrLy 1570       1580       1590       1600       1610       1620
GTATGGTGATCCAGACCATTATTCTAAGCGTTACACTGGTTCAAGTGATAACGGTGGCGT
sTyrGlyAspProAspHisTyrSerLysArgTyrThrGlySerSerAspAsnGlyGlyVa 1630       1640       1650       1660       1670       1680
TCATACAAACAGCGGCATTATTAATAAACAAGCTTATTTATTAGCAAATGGCGGTACGCA
lHisThrAsnSerGlyIleIleAsnLysGlnAlaTyrLeuLeuAlaAsnGlyGlyThrHi
```

FIGURE 2C

```
         1690      1700      1710      1720      1730      1740
     TTACGGTGTAACTGTAAATGGTATCGGCAAAGATAAATTAGGTGCGATTTACTACCGTGC
     sTyrGlyValThrValAsnGlyIleGlyLysAspLysLeuGlyAlaIleTyrTyrArgAl 1750      1760      1770      1780      1790      1800
     AAATACACAGTATTTCACGCAATCTACTACATTTAGTCAAGCTCGTGCTGGTGCAGTACA
     aAsnThrGlnTyrPheThrGlnSerThrThrPheSerGlnAlaArgAlaGlyAlaValGl 1810      1820      1830      1840      1850      1860
     AGCTGCAGCAGACTTATATGGTGCAAATTCTGCTGAAGTAGCAGCAGTTAAGCAATCATT
     nAlaAlaAlaAspLeuTyrGlyAlaAsnSerAlaGluValAlaAlaValLysGlnSerPh 1870      1880      1890      1900      1910      1920
     TAGTGCTGTTGGTATTAACTAAGGACTTAACGGATAGCTATTAATAAAATACCTCAAAAA
     eSerAlaValGlyIleAsnEnd 1930      1940      1950      1960
     TAAAGAAGGAGCCTATGCTCCTTCTTTATTTTTTTCTCCA
```

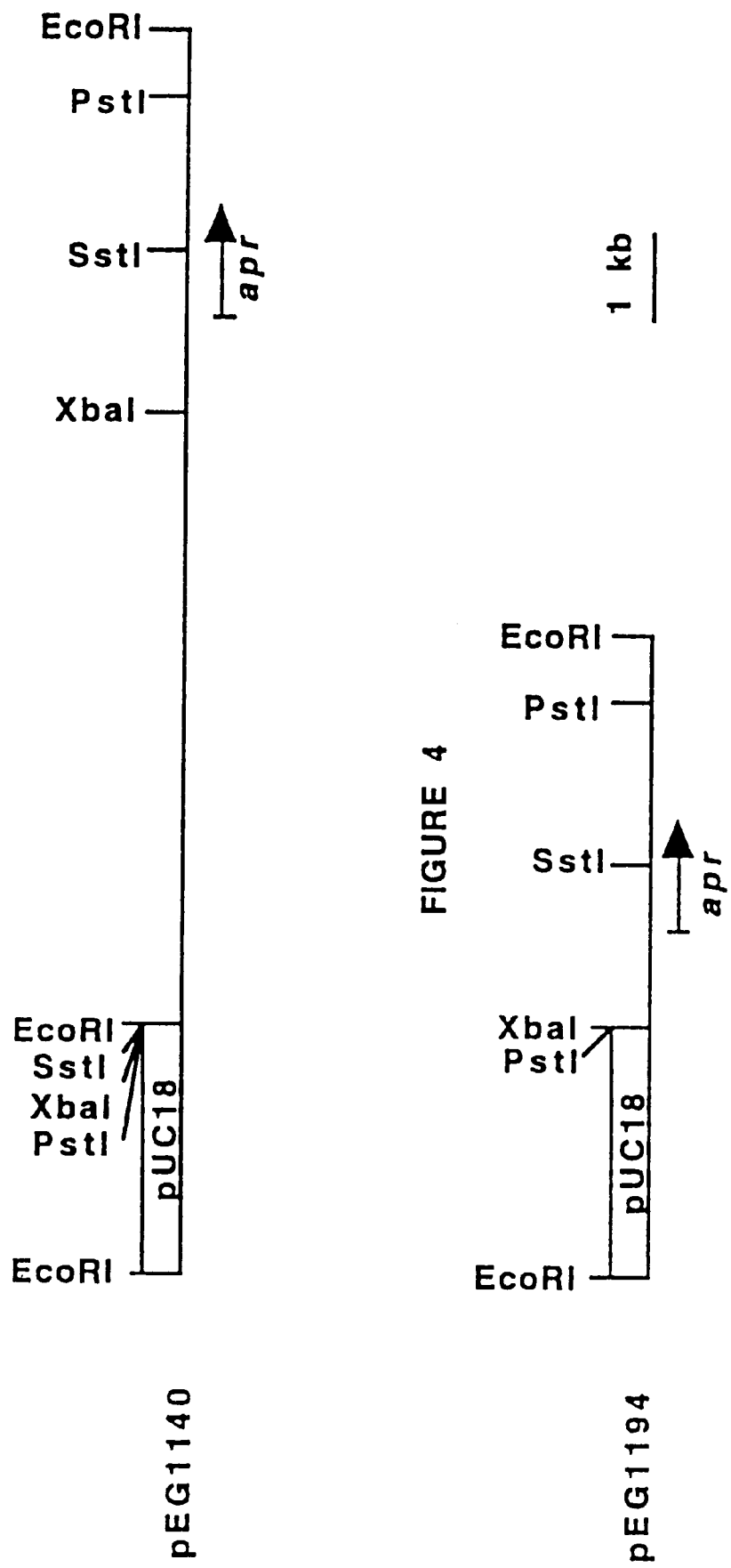

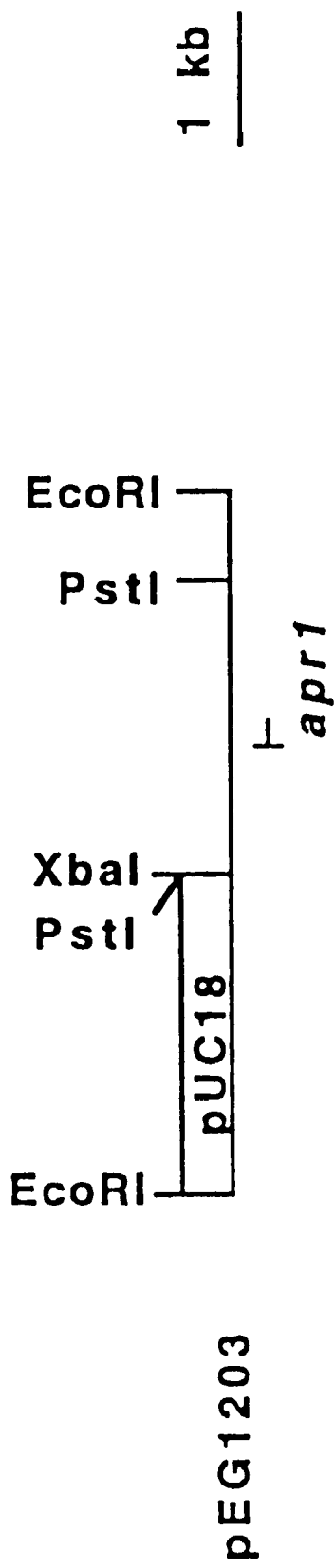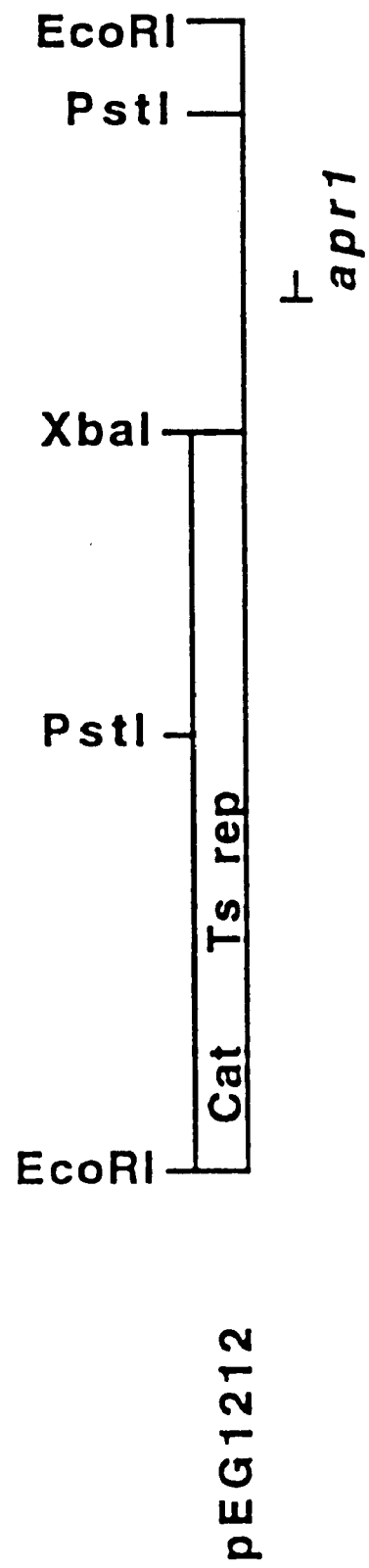

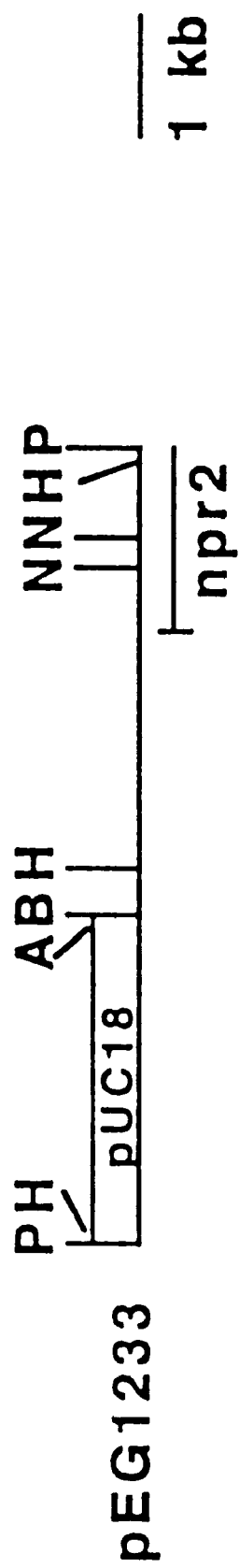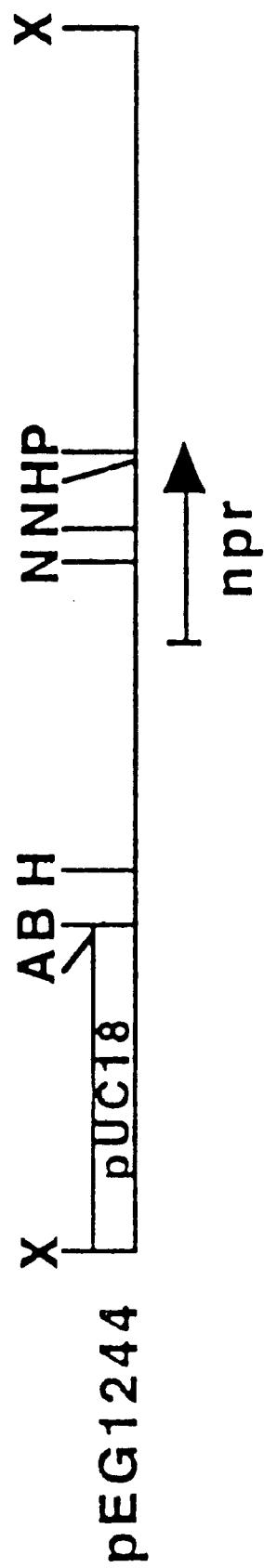

METHOD OF REDUCING THE PROTEOLYTIC DEGRADATION OF *BACILLUS THURINGIENSIS* INSECTICIDAL TOXIC PROTEIN

CROSS-REFERENCE TO RELATED APPLICATION

This application is a division of U.S. patent application Ser. No. 08/415,823, filed Mar. 31, 1995, now U.S. Pat. No. 5,759,538.

FIELD OF THE INVENTION

The present invention relates to an alkaline protease gene (apr) and a neutral protease gene (npr) derived from a *Bacillus thuringiensis* (B.t.) strain, genetically disabled apr and npr genes, insecticidal B.t. strain constructs containing a genetically disabled apr gene and/or npr gene, an insecticide composition containing the disabled genes or the constructs including the disabled genes, and a method for using the disabled genes and their constructs.

BACKGROUND OF THE INVENTION

*Bacillus thuringiensis* ( "B.t.") is a gram-positive soil bacterium that produces proteinaceous crystalline inclusions during sporulation. These B.t. crystal proteins are often highly toxic to specific insects. Insecticidal activities have been identified for crystal proteins from various B.t. strains against insect larvae from the insect orders Lepidoptera (caterpillars), Diptera (mosquitos, flies) and Coleoptera (beetles).

Recently, certain B.t. strains and B.t. crystal proteins have been reported as having activity against non-insect species such as nematodes. The term "insecticidal," as used herein with reference to B.t. strains and their crystal proteins, is intended to include such pathogenic activities against non-insect species.

Individual B.t. crystal proteins, also called delta-endotoxins or parasporal crystals or toxin proteins, can differ extensively in their structure and insecticidal activity. These insecticidal proteins are encoded by genes typically located on large plasmids, greater than 30 megadaltons (mDa) in size, that are found in B.t. strains. A number of these B.t. toxin genes have been cloned and the insecticidal crystal protein products characterized for their specific insecticidal properties. A good review of cloned B.t. toxin genes and crystal proteins is given by Höfte et al., *Microbiol. Rev.* 53:242–255 (1989), who also propose a useful nomenclature and classification scheme that has been adopted here.

The insecticidal properties of B.t. have been long recognized, and B.t. strains have been incorporated in commercial biological insecticide products for over thirty years. Commercial B.t. insecticide formulations typically contain dried B.t. fermentation cultures whose crystal protein is toxic to various insect species.

Traditional commercial B.t. bioinsecticide products are derived from "wild-type" B.t. strains, i.e., purified cultures of B.t. strains isolated from natural sources. Newer commercial B.t. bioinsecticide products are based on genetically altered B.t. strains, such as the transconjugant B.t. strains described in U.S. Pat. No. 5,080,897 issued to Gonzalez, Jr., et al. on Jan. 14, 1992, and in U.S. Pat. No. 4,935,353 issued to Burges et al. on Jun. 19, 1990.

Recombinant B.t. strains, with novel complements of B.t. toxin genes providing wide spectrum and/or enhanced insecticidal activity, are likely to be incorporated into commercial B.t. bioinsecticides in the foreseeable future.

All B.t.-based bioinsecticides have the advantage of being selectively toxic to specific target insect species without exhibiting any toxicity towards vertebrates. A drawback to B.t. bioinsecticides is that the persistence of insecticidal activity is limited. The insecticidal half-life of B.t. bioinsecticides is typically less than one week in duration, even with protective adjuvants that are typically employed in commercial B.t. formulations.

Studies on loss of insecticidal activity in B.t. proteins have identified solar irradiation as a cause and have recommended the use of photoprotectants in B.t. formulations; see, for example, Pozsgay et al., *J. Invertebr. Pathol.* 50:246–253 (1987) and Morris, *Canadian Entomol.* 115:1215–1227 (1983): Cell encapsulation and cell treatment technologies such as described in U.S. Pat. Nos. 4,695,455 and 4,695,462, both issued to Barnes et al. on Sep. 22, 1987, have also been employed to protect the insecticidal toxin activity of the B.t. protein against environmental factors.

It has long been recognized that the insecticidal activity of B.t. proteins is induced, at least in part, by the action of proteolytic enzymes on B.t. protein which has been ingested by a susceptible insect species. Höfte et al., *Microbiol. Rev.* 53:242–255 (1989), note that B.t. crystalline protein dissolves in the larval insect midgut and that many of these B.t. proteins are protoxins that are proteolytically converted into smaller toxic polypeptides, i.e., activated toxin, in the insect midgut.

Researchers have reported the existence of proteases in B.t., but the role of these proteases in the insecticidal activity of B.t. proteins or, more generally, in the physiology of B.t. is unclear because of the contradictory results reported.

The role of B.t. proteases in B.t. protein solubilization is described by Chestukhina et al., *Biokhimiya* 43:857–864 (1978), who carried out dissolution studies with B.t. crystalline proteins and concluded that degradation of B.t. proteins during dissolution was facilitated by the presence of serine proteases, metalloproteases and leucine antipeptidase in the B.t. crystal protein. Similarly, Thurley et al., *FEMS Microbiol. Lett.* 27:221–225 (1985), reported that a cystein-like crystal-associated protease assisted in the solubilization of a B.t. crystal protein.

A role of B.t. proteases in insecticidal activity is described by Chilcott et al., *FEMS Microbiol. Lett.* 18:37–41 (1983), who reported that two different proteolytic activities were associated with B.t. crystal protein and that B.t. with reduced proteolytic activity exhibited lower insect toxicity. Bulla, Jr. et al., *J. Bacteriol.* 130:375–383 (1977), likewise concluded that B.t. crystal proteins have an autolytic activity which apparently involves a sulfhydryl protease that is activated under alkaline conditions (such as found in an insect midgut) and that renders the B.t. protein insecticidal.

An opposite conclusion was reached by Pfannensteil et al., *FEMS Microbiol. Lett.* 21:39–42 (1984), who reported that B.t. crystal protein treated to reduce the crystal-associated protease activity exhibited no difference in insecticidal activity from the untreated crystal protein (which was from the same B.t. subspecies as that of Chilcott et al.). A similar conclusion was reached by Bibilos et al., *Canad. J. Microbiol.* 34:740–747 (1988) who described the role of B.t. proteases, primarily neutral metalloproteases, in effecting activation of B.t. protein protoxin to active toxin, but concluded that this is unnecessary, since the same result is accomplished in the insect midgut, presumably by insect-derived proteases.

In contrast to the results reported by Chilcott et al. and Pfannensteil et al., Pearson et al., *J. Appl. Bacteriol.*

65:195–202 (1988), proposed a negative role for B.t. proteases in the insecticidal activity of B.t. crystal protein. Pearson et al. concluded that more than one type of protease was present in B.t. crystal protein produced by sporulated, lysed B.t. cells and that a decline of insecticidal activity might be associated with proteolytic action.

Some B.t. proteases have been identified, at least in part, in the literature. Li et al., *Applied Microbiol.* 39:354–361 (1975), describe a partially purified extracellular metalloprotease from B.t. having a molecular mass of about 38 kilodaltons (kDa). Lecadet et al., *Eur. J. Biochem.* 79:329–338 (1977), describe an extracellular serine protease from B.t. having a molecular mass of about 23 kDa. Stepanov et al., *Biochem. Biophys. Res. Comm.* 100:1680–1687 (1981), disclose the N-terminal amino acid sequence of a purified extracellular serine protease from B.t. Kunitate et al., *Agric. Biol. Chem.* 53:3251–3256 (1989), describe a purified SH-containing serine protease from B.t. whose N-terminal sequence was similar to that reported by Stepanov et al. for their purified protease.

An isolated, cloned B.t. protease gene is described by Lovgren et al., *Molecul. Microbiol.* 4:2137–2146 (1990), who report the nucleotide sequence of a B.t. derived gene that encodes a neutral metalloprotease, which was found to be toxic when injected into a lepidopteran insect.

The nucleotide sequence of the promoter region of a B.t. protease gene is disclosed by Geiser in PCT International Patent Publication No. WO 92/14826 dated Sep. 3, 1992, of Ciba-Geigy AG, where the promoter is operatively linked with a heterologous gene, such as β-galactosidase.

Although the published literature on the cloning and characterization of B.t.-derived protease genes is limited, much work has been carried out on identifying proteases and protease genes in other Bacillus species, particularly *Bacillus subtilis*: see Pero et al., "Proteases" in *Bacillus subtilis and other Gram-Positive Bacteria, Amer. Soc. Microbiol.*, Washington, D.C., 1993, pages 939–952. The cloning of the subtilisin gene of *B. subtilis*, which encodes an alkaline protease (also called subtilisin or serine protease), is reported by Stahl et al., *J. Bacteriol.* 158:411–418 (1984). Another *B. subtilis* protease gene, one that encodes a neutral metalloprotease, was cloned by Yang et al., *J. Bacteriol.* 160:15–21 (1984), who used a deleted version of the neutral protease gene to displace the wild-type neutral protease gene in *B. subtilis*. Proteolytic activity in the mutant was only 20% of the wild-type strain, and another mutant, deleted in both the alkaline protease gene and the neutral protease gene, produced no detectable levels of proteolytic activity. A major extracellular protease of *Bacillus cereus* was purified by Sidler et al., *Biol. Chem. Hoppe-Seyler* 367:643–657 (1986), who reported the N-terminal amino acid sequence to be 45% homologous to that of the *B. subtilis* neutral protease.

U.S. Pat. No. 4,828,994, issued to Fahnestock et al. on May 9, 1989, discloses production of genetically altered strains of *Bacillus subtilis*, which is rendered incapable of synthesizing the proteolytic enzyme subtilisin by replacing the native chromosomal DNA comprising the subtilisin gene with a DNA sequence comprising a subtilisin gene which has an inactivating DNA sequence inserted therein. The purpose is to insert into the subtilisin gene a functional gene coding for a protein which confers a phenotypic trait, such as resistance to a selected antibiotic to facilitate identification of the altered microorganism and subsequent transfer of the inactivated gene into other bacterial strains. "Subtilisin" as used by Fahnestock et al. refers to the enzyme alkaline serine protease, without regard to the species of Bacillus in which it is produced.

U.S. Pat. No. 4,766,077, issued to Orser et al. on Aug. 23, 1988, relates to a method for modifying ice nucleation bacteria in vitro to confer an ice nucleation deficient phenotype. Modification is accomplished by deletion, substitution, insertion, inversion or transversion of a DNA segment within the gene locus responsible for the ice nucleation phenotype. The mutations are limited to the particular gene locus so that the modified microorganisms are genetically stable and free from random mutations which might adversely affect their competitive fitness. The modified microorganisms are useful for prevention of frost damage to susceptible plant hosts.

SUMMARY OF THE INVENTION

The present invention is based on the discovery, isolation, sequencing and characterization of two protease genes present in B.t. One is an alkaline protease gene generally designated "apr." The other is a neutral protease gene generally designated "npr." The invention also includes genetically disabling the apr and the npr genes to reduce proteolytic activity of the protease encoded by the genes, and using the disabled genes in insecticidal B.t. constructs along with one or more B.t. protein toxin genes. These resulting B.t. constructs are useful for the enhanced production of B.t. toxin protein. The B.t. toxin protein recovered from the fermentation production of these B.t. constructs also exhibits improved stability with respect to its insecticidal activity.

One aspect of the present invention relates to a B.t. protease gene disabled from coding for protease capable of degrading B.t. insecticidal toxic protein, whereby protease expressed by an organism containing the disabled protease gene has reduced proteolytic activity against the toxic protein compared to protease encoded by a counterpart protease gene that has not been disabled.

Another aspect of the present invention relates to a recombinant construct comprising a cloned gene encoding a B.t. insecticidal toxic protein and a disabled B.t. protease gene disabled from coding for protease capable of degrading B.t. insecticidal toxic protein, whereby protease expressed by an organism containing the disabled protease gene has reduced proteolytic activity against the toxic protein compared to protease encoded by a counterpart protease gene that has not been disabled.

Still another aspect of the present invention relates to a method of reducing the proteolytic degradation of a B.t. insecticidal toxic protein in a composition comprising the toxic protein, the method comprising including in the composition a B.t. protease gene disabled from coding for protease capable of degrading the toxic protein, whereby protease expressed by an organism within the composition containing the disabled protease gene has reduced proteolytic activity against the toxic protein compared to protease encoded by a counterpart protease gene that has not been disabled, thereby resulting in reduced proteolytic activity against the toxic protein.

BRIEF DESCRIPTION OF THE DRAWINGS

FIG. 1 consists of FIGS. 1A and 1B and depicts the nucleotide sequence for the apr gene, the B.t. alkaline protease gene (SEQ ID NO:1) of this invention. The deduced amino acid sequence of the Apr alkaline protease protein (SEQ ID NO:2), encoded by the open reading frame extending from nucleotide base positions 225 to 1415

(excluding the. terminal stop codon), is also shown. The restriction endonuclease cleavage site for SstI at nucleotide position 954 within the apr gene is also shown.

FIG. 2 consists of FIGS. 2A through 2C and depicts the nucleotide sequence for the npr gene, the B.t. neutral protease gene (SEQ ID NO:3) of this invention. The deduced amino acid sequence of the Npr neutral protease protein (SEQ ID NO:4), encoded by the open reading frame extending from nucleotide base positions 182 to 1879 (excluding the terminal stop codon), is also shown. The restriction endonuclease cleavage sites for NdeI within the npr gene are also shown.

FIG. 3 is a linear structural map of plasmid pEG1140, a 14.7 kilobase (kb) plasmid containing the cloned apr gene on a 12 kb EcoRI DNA fragment inserted into plasmid vector pUC18, shown by the labeled open segment. The location and orientation of the apr gene are shown by the arrow. Locations of various restriction endonuclease cleavage sites are shown in this Figure and in subsequent Figures.

FIG. 4 is a linear structural map of plasmid pEG1194, a 7.1 kb plasmid that contains the wild type apr gene on a 4.3 kb XbaI-EcoRI DNA fragment subcloned from plasmid pEG1140 (FIG. 3) into plasmid vector pUC18, shown by the labeled open segment. The short line segment marked "1 kb" to the right of the linear structural map in FIG. 4 indicates the approximate size of 1 kilobase for the linear structural maps of FIGS. 3 and 4.

FIG. 5 is a linear structural map of plasmid pEG1203, a 6.2 kb plasmid containing a genetically disabled apr gene designated as the "apr1" allele, on a 3.1 kb XbaI-EcoRI DNA fragment inserted into plasmid vector pUC18, shown by the labeled open segment. The short line segment marked "1 kb" to the right of the linear structural map in FIG. 5 indicates the approximate size of 1 kilobase for the linear structural maps shown in FIGS. 5 and 6.

FIG. 6 is a linear structural map of plasmid pEG1212, a 10.3 kb plasmid that was derived from plasmid pEG491 into which the 3.1 kb XbaI-EcoRI apr1-containing DNA fragment of plasmid pEG1203 (FIG. 5) was subcloned. The open segment of plasmid pEG1212 represents plasmid pEG491, which contains an antibiotic resistance marker gene, chloramphenicol acetyl transferase (Cat), and a temperature sensitive Bacillus replicon (Ts rep).

Figure 7:
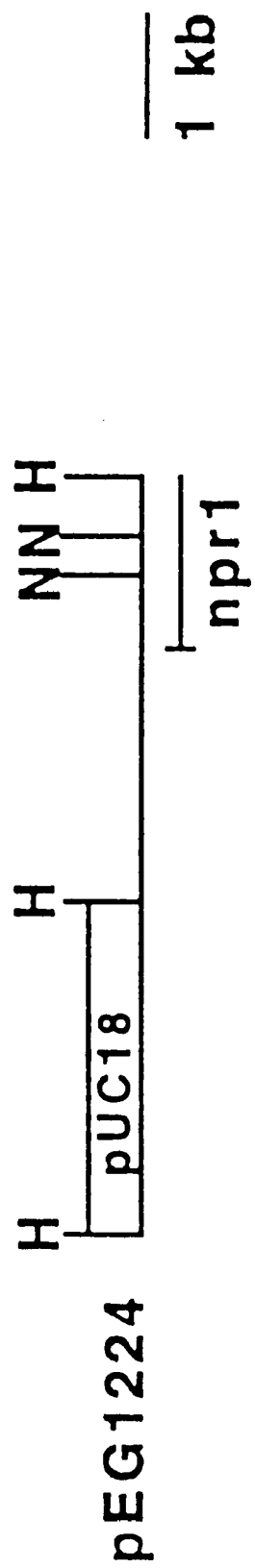

FIG. 7 is a linear structural map of plasmid pEG1224, a 6.2 kb plasmid that contains a truncated portion of the open reading frame of the npr gene, designated as the "npr1" allele, on a 3.4 kb HindIII DNA fragment inserted into plasmid vector pUC18, shown by the labeled open segment. The location of the npr1 allele is shown. The short line segment marked "1 kb" to the right of the linear structural map in FIG. 7 indicates the approximate size of 1 kilobase in the linear structural maps shown in FIGS. 7 and 8.

In FIGS. 7 through 14, restriction sites are indicated by: H=HindIII, N=NdeI, P=PstI, B=BamHI, A=Asp718, X=XbaI, R=EcoRI, and MCS=multiple cloning site containing sites for Asp718 and PstI.

Figure 8:
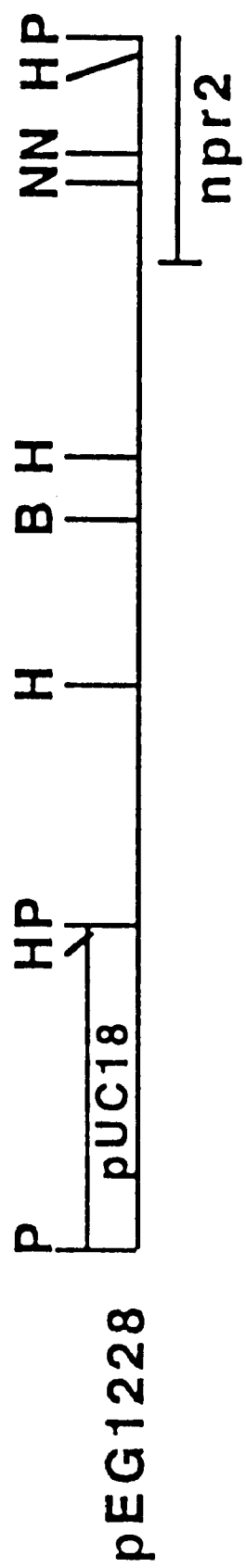

FIG. 8 is a linear structural map of plasmid pEG1228, an 11.6 kb plasmid that contains another truncated portion of the npr gene, designated as the "npr2" allele, on an 8.0 kb PstI DNA fragment inserted into plasmid vector pUC18, shown by the labeled open segment.

FIG. 9 is a linear structural map of plasmid pEG1233, a 6.6 kb plasmid that contains the npr2 allele on a 3.9 kb BamHI-PstI DNA fragment, subcloned from plasmid pEG1228 (FIG. 8) into plasmid vector pUC18, shown by the labeled open segment. The short line segment marked "1 kb" to the right of the linear structural map in FIG. 9 indicates the approximate size of 1 kilobase in the linear structural maps shown in FIGS. 9 and 10.

FIG. 10 is a linear structural map of plasmid pEG1244, a 10.2 kb plasmid containing the cloned npr gene, with its entire open reading frame, on a 7.5 kb BamHI-XbaI DNA fragment inserted into plasmid vector pUC18, shown by the labeled open segment.

Figure 11:
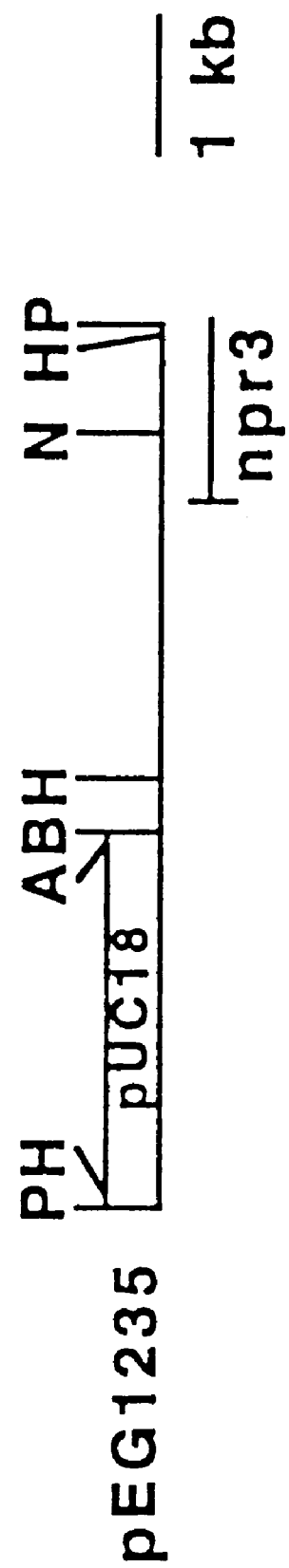

FIG. 11 is a linear structural map of plasmid pEG1235 a 6.4 kb plasmid that contains a genetically disabled version of the npr gene, designated as "npr3", on a 3.7 kb BamHI-PstI DNA fragment, derived from NdeI digestion and religation of plasmid pEG1233 (FIG. 9). The short line segment marked "1 kb" to the right of the linear structural map in FIG. 11 indicates the approximate size of 1 kilobase in the linear structural maps shown in FIGS. 11 and 12.

Figure 12:
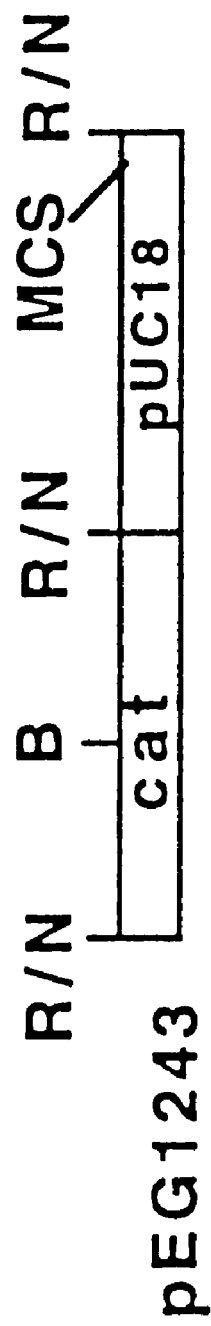

FIG. 12 is a linear structural map of plasmid pEG1243, a 5.7 kb plasmid containing a 2.8 kb EcoRI DNA fragment from plasmid pNN101 blunt-end ligated into the NdeI site of plasmid vector pUC18, shown by the labeled open segment. The location of a chloramphenicol antibiotic resistance marker gene, chloramphenicol acetyl transferase (Cat), contained on the pNN101-derived segment, is also shown. "R/N" indicates the ligation of EcoRI and NdeI sites, "MCS" indicates a multiple cloning site in the pUC18 DNA segment and "cat" indicates the approximate location of the Cat antibiotic resistance marker gene in the 2.8 kb EcoRI fragment from plasmid pNN101.

Figure 13:
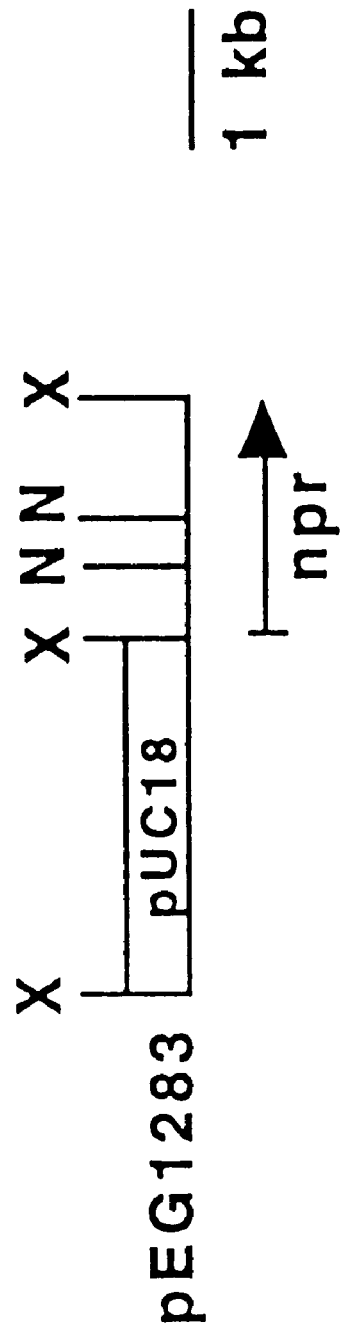

FIG. 13 is a linear structural map of plasmid pEG1283, a 4.5 kb plasmid that contains the npr gene within a 1.7 kb XbaI DNA restriction fragment ligated into the XbaI site of plasmid vector pUC18. The 1.7 kb DNA fragment contains only the coding region of the npr gene beginning at nucleotide 182 and ending at nucleotide 1882 as shown in FIG. 2. The short line segment marked "1 kb" to the right of the linear structural map in FIG. 13 indicates the approximate size of 1 kilobase in the linear structural maps shown in FIGS. 13 and 14.

Figure 14:
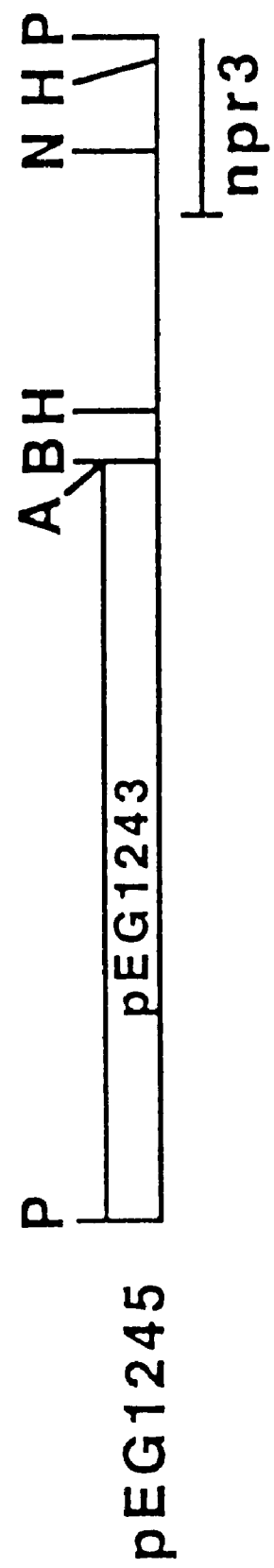

FIG. 14 is of a linear structural map of plasmid pEG1245, a 9.4 kb plasmid that contains the npr3 allele on a 3.7 kb Asp718-PstI DNA fragment subcloned from plasmid pEG1235 (FIG. 11) into the Asp718-PstI sites of plasmid pEG1243 (FIG. 12), shown by the labeled open rectangular segment in FIG. 14.

MICROORGANISM DEPOSITS

To assure the availability of materials to those interested members of the public upon issuance of a patent on the present application, deposits of the microorganism listed in the following Table 1 were made prior to filing the present application with the ARS Patent Collection, Agricultural Research Service Culture Collection (NRRL), 1815 North University Street, Peoria, Ill. 61604.

These microorganism deposits were made under the provisions of the "Budapest Treaty on the International Recognition of the Deposit of Microorganisms for the Purpose of Patent Procedure." All restrictions on the availability to the public of these deposited microorganisms will be irrevocably removed upon issuance of a United States patent based on this application.

TABLE 1

| Cell Type | Strain | Recombinant Plasmid | NRRL Accession Number | Date of Deposit |
|---|---|---|---|---|
| B. t. | EG2371 | none | NRRL B-18209 | 23 Apr '87 |
| B. t. | EG7283 | pEG1111 (cryET5⁺ apr⁺) | NRRL B-21111 | 9 Jun '93 |
| B. t. | EG10368 | none | NRRL B-21125 | 30 Jun '93 |
| E. coli | EG7940 | pEG1194 (apr⁺) | NRRL B-21342 | 11 Oct '94 |
| B. t. | EG7950 | pEG1212 (apr1) | NRRL B-21343 | 11 Oct '94 |
| B. t. | EG10654 | none | NRRL B-21344 | 11 Oct '94 |
| E. coli | EG7978 | pEG1233 (npr2) | NRRL B-21345 | 11 Oct '94 |
| E. coli | EG11447 | pEG1245 (npr3) | NRRL B-21346 | 11 Oct '94 |
| B. t. | EG10624 | none | NRRL B-21347 | 11 Oct '94 |
| E. coli | EG11466 | pEG1283 (npr⁺) | NRRL B-21358 | 29 Nov '94 |

DETAILED DESCRIPTION OF THE PREFERRED EMBODIMENTS

The present invention is based on the discovery, identification, isolation, sequencing, characterization, genetic disablement and use of the alkaline protease gene ("apr") (SEQ ID NO:1), and the neutral protease gene ("npr") (SEQ ID NO:3) from B.t. While the presently preferred embodiment of the apr and npr genes, disabled genes based upon them and proteins encoded by them are derived from B.t. strain EG2371, the present invention is not so limited in scope. It is believed, based on the study set forth in Example 17 below that the apr and npr protease genes isolated and sequenced herein are found in a great many other subspecies or varieties of B.t. bacteria.

The present invention covers those gene nucleotide base sequences that encode the amino acid sequences of the indicated proteins, since variations may be made in the nucleotide base sequences which do not affect the amino acid sequence of the gene product, since the degeneracy of the genetic code is well known to those skilled in the art. Moreover, there may be some variations, including deletions, additions, substitutions, inversions or truncations in the coding region of the nucleotide base sequence which allow expression of the respective genes and production of functionally equivalent forms of the insecticidal crystal proteins or proteases as desired. Thus, these types of non-disabling mutants, variants, homologs, recombinant or genetically engineered derivatives thereof, which may be determined without undue experimentation by those of ordinary skill in the art with reference to the present specification, are to. be considered within the scope of the appended claims, since they are fully equivalent to the specifically disclosed and claimed subject matter.

It has been shown that proteins of identical structure and function may be constructed by changing the amino acid sequence, if such changes do not alter the protein secondary structure (Kaiser and Kezdy, Science, 223, pp. 249–255 (1984)). Single amino acid substitutions have been introduced by site-directed mutagenesis at various position of CryIA(a) toxin protein without altering the insecticidal properties of the parent toxin (Ge et al., Proc. Natl. Acad. Sci. USA, 86, pp. 4037–4041 (1989). The present invention includes mutants of the amino acid sequences disclosed herein which have an unaltered protein secondary structure or, if the structure is altered, where the substantially equivalent biological activity is retained in the mutant or derivative.

The foregoing types of non-disabling modification, mutation, variation must be and hereby are distinguished from those modifications to the apr or npr genes that are specifically intended to disable the gene from encoding protease which could adversely affect the beneficial insecticidal toxic crystal proteins used in pest control. Thus, an important aspect of the present invention is the intentional selective disabling modification of the protease genes, as set forth below.

The apr gene encodes the B.t. alkaline protease protein Apr (SEQ ID NO:2). The npr gene encodes the B.t. neutral protease protein Npr (SEQ ID NO:4). The apr gene was cloned from B.t. strain EG2371 using the gene specific oligonucleotide WD168 (SEQ ID NO:5). The npr gene was cloned from B.t. strain EG2371 using the gene specific oligonucleotides WD205 (SEQ ID NO:6) and WD206 (SEQ ID NO:7).

While the identification, isolation and sequencing of the apr and npr genes and their associated Apr and Npr proteins are important first steps in the present invention, the primary value of the present invention is the subsequent discovery that both the apr and npr genes may be disabled (as described in detail in illustrative Examples 2, 3, 11 and 12) to the extent that microorganisms containing them exhibit markedly lower proteolytic activity with respect to counterpart microorganisms containing non-disabled protease genes (as described in detail in illustrative Examples 4 and 13). The result of the reduced proteolytic activity is that the microorganisms containing both insecticidal crystal toxic protein genes and the disabled protease genes are capable of producing higher levels of insecticidal crystal proteins (as described in detail in illustrative Examples 5, 8 and 14) and are capable of producing crystal proteins having increased stability during storage (as described for instance in Examples 9 and 15). The basis for the increased crystal protein production and stability is the fact that proteases degrade proteins. The insecticidal activity of the strains containing the disabled protease genes is not adversely affected and may be enhanced (as described in detail in illustrative Examples 6 and 16).

Based on the foregoing research, the present invention is directed to a B.t. protease gene disabled from coding for protease capable of degrading B.t. insecticidal toxic protein, whereby protease expressed by an organism containing the disabled protease gene has reduced proteolytic activity against the toxic protein compared to protease encoded by a counterpart protease gene that has not been disabled.

There are two preferred protease genes with respect to the present invention, although the concept of the present invention is believed to be applicable to any B.t. protease genes.

One presently preferred protease gene is the apr gene having the nucleotide base sequence illustrated in FIG. 1 and set forth in SEQ ID NO:1, or any equivalent, non-disabled modified mutant, derivative or recombinant thereof capable, when not disabled, of encoding the Apr alkaline protease protein having a deduced amino acid sequence of 397 amino acids as illustrated in FIG. 1 and set forth in SEQ ID NO:2, with a molecular mass of 42,339 Da. The apr gene was cloned, isolated and sequenced as set forth in Example 1 below.

Another presently preferred protease gene is the npr gene having the nucleotide base sequence illustrated in FIG. 2 and set forth in SEQ ID NO:3, or any equivalent, non-disabled modified mutant, derivative or recombinant thereof capable, when not disabled, of encoding the Npr neutral protease protein having a deduced amino acid sequence of 566 amino acids as illustrated in FIG. 2 and set forth in SEQ ID NO:4, with a molecular mass of 60,982 Da. The npr gene was cloned, isolated and sequenced as set forth in Example 10 below.

Once the desired protease genes are identified and characterized, they are modified in a manner to intentionally disable their ability to effectively code for protease. Thus, the disabling modification should render protease produced by the microorganism containing the disabled protease genes less proteolytically active against the desirable toxic proteins produced by the microorganism than a counterpart protease gene that has not been disabled.

The present invention also relates to a method for disabling the apr gene so that strains of B.t. containing the disabled gene produce an increased level of crystal protein. The method comprises cloning and sequencing the apr gene, deleting an essential portion of the cloned apr gene in vitro, yielding the disabled apr1 allele. See illustrative Example 2. A plasmid vector containing the disabled apr1 allele may then be constructed and subsequently used to disable the apr gene in vivo, as explained in illustrative Example 3. Since many varieties of B.t. contain the wild-type apr gene, as demonstated amply in Example 17, the apr gene in all of these varieties can be disabled in vivo as described herein to enhance the production of their respective insecticidal crystal proteins. The plus symbol ("+") following a gene signifies the presence of the wild-type gene. A minus symbol ("−") signifies the absence of a phenotype (e.g., EG10368 Cry$^-$ apr$^+$ indicates absence of crystal toxin proteins and the presence of the wild-type apr gene).

Similarly to the apr gene, the cloned, disabled npr gene, designated the "npr3" allele, can be used to disable the npr gene in many B.t. strains. A method of doing so includes cloning and sequencing the npr gene, deleting an essential portion of the cloned npr gene in vitro to yield the npr3 allele. See illustrative Example 11. The npr3 allele is capable of disabling the npr gene in vivo, as set forth in illustrative Example 12. Since many varieties of B.t. contain the wild-type npr$^+$ gene, as demonstrated in Example 17, in all varieties containing the npr$^+$ gene, the npr$^+$ gene can be disabled in vivo in the manner described hereinafter.

While Examples 2 and 11 respectively describe specific in vitro deletions of certain portions of the DNA sequences of the apr and npr genes yielding the apr1 and npr3 alleles, respectively, there are a number of other ways in which the apr and npr genes can be effectively disabled in a manner that will reduce their proteolytic activity.

An example of an effective disabling modification would be a single nucleotide deletion occurring at the beginning of either the apr or npr gene that would produce a translational reading frameshift. Such a frameshift would disable the apr or npr gene. Protease production by the gene could be disrupted if the regulatory regions or the coding regions of the protease genes are disrupted.

A goal is to disrupt and eliminate the production of protease so that the B.t. insecticidal crystal protein toxins will not be degraded by the proteases. This results in increased yield of the insecticidal crystal protein toxins and their enhanced stability in the absence of proteases which would otherwise degrade them.

In addition to disabling the apr and npr genes by deleting nucleotides, causing a transitional reading frameshift, disabling proteolytic modifications would also be possible by other techniques including insertions, substitutions, inversions or transversions of nucleotides within the gene's DNA that would effectively prevent the formation of proteases that would degrade the desirable B.t. insecticidal crystal protein toxins.

It is also within the capabilities of one skilled in the art to disable the apr and npr genes by the use of less specific methods. Examples of less specific methods would be the use of chemical mutagens such as hydroxylamine or nitrosoguanidine or the use of radiation mutagens such as gamma radiation or ultraviolet radiation to randomly mutate genes in B.t. strains. Such mutated B.t. strains could, by chance, contain disabled apr and npr genes such that the genes were no longer capable of producing protease proteins. The presence of the desired disabled genes could be detected by routine screening techniques.

Another aspect of the present invention relates to a recombinant construct comprising a gene encoding a B.t. insecticidal toxic protein and a disabled B.t. protease gene disabled from coding for protease capable of degrading B.t. insecticidal toxic protein, whereby protease expressed by an organism containing the disabled protease gene has reduced proteolytic activity against the toxic protein compared to protease encoded by a counterpart protease gene that has not been disabled. Examples 8 and 14 provide illustrative explanations of such constructs involving the disabled apr1 and npr3 genes, respectively.

Moreover, while Examples 8 and 14 demonstrate the utility of the disabled protease genes and the formation of illustrative recombinant constructs containing them with only a few exemplary insecticidal toxic crystal protein genes and their associated toxic proteins, the present invention is not so limited. Thus, for example, substantially all known and, it is believed, even yet to be discovered toxic proteins and/or their genes could be used effectively in recombinant constructs including disabled protease genes. Non-limiting examples of such toxic proteins are CryI-type, CryII-type, CryIII-type, CryIV-type, CryV-type, CryET1, Cry ET4 and CryET5 protein, and mixtures thereof. These are all well documented and available insecticidal toxic proteins, encoded by the following respective genes, all of which are also known and available: cryI-type, cryII-type, cryIII-type, cryIV-type, cryV-type, cryET1, cryET4 and cryET5 genes, and mixtures thereof.

Still another aspect of the present invention relates to a method of reducing the proteolytic degradation of a B.t. insecticidal toxic protein in a composition comprising the toxic protein, the method comprising including in the composition a B.t. protease gene disabled from coding for protease capable of degrading the toxic protein, whereby protease expressed by an organism within the composition containing the disabled protease gene has reduced proteolytic activity against the toxic protein compared to protease encoded by a counterpart protease gene that has not been disabled, thereby resulting in reduced proteolytic activity against the toxic protein.

To perform the foregoing method, one skilled in the art and familiar with this disclosure would merely apply its teachings of how to make and use the disabled protease genes and B.t. constructs as described herein.

Alternatively, one skilled in the art could use the methods of chemical mutagenesis or radiation mutagenesis to randomly mutate B.t. strains and thus by chance disable protease genes. A significant disadvantage of these random mutagenesis methods is that with these methods, genes other than the ones encoding specific protease proteins would also likely be mutated. In contrast to random methods of mutagenesis, the methods described herein are completely specific for disabling only the apr and npr genes and no other genes are affected.

Once the proteolytically modified genes have been created, they can be included in cultures and other formulations typically used to produce B.t. insecticidal crystal protein toxins. The usual production of such toxins would not be affected adversely by the presence of the disabled genes and, to the contrary, due to the reduced proteolytic activity, crystal protein toxin production is enhanced.

The resulting crystal protein toxins can be used as the active ingredient insecticidal formulations or compositions. Likewise, the recombinant constructs or strains of the present invention or even the disabled protease genes of the present invention could be incorporated into any desired insecticidal compostion. Such insecticidal formulations or compositions typically contain agriculturally acceptable carriers or adjuvants in addition to the active ingredient and are prepared and used in a manner well known to those skilled in the art.

The crystal protein toxins may be employed in insecticidal formulations in isolated or purified form, e.g., as the crystal protein itself. Alternatively, they may be present in the recovered fermentation solids, obtained from culturing of a Bacillus strain, e.g., *Bacillus thuringiensis* or other microorganism host carrying the appropriate gene capable of producing the desired crystal protein. The crystal protein is usually associated with the B.t. bacterium which produced the protein, as an intimate mixture of crystal protein, cell debris and spores, if any, in the recovered fermentation solids. The recovered fermentation solids containing the crystal protein may be dried, if desired, prior to incorporation in the insecticidal formulation. Genetically engineered or transformed B.t. strains or other host microorganisms containing a recombinant plasmid that expresses a cloned toxin gene to produce the desired protein toxin, obtained by recombinant DNA procedures, may also be used.

The formulations or compositions of this invention containing the insecticidal protein as the active component are applied at an insecticidally effective amount which will vary depending on such factors as, for example, the specific insects to be controlled, the specific plant or crop to be treated and the method of applying the insecticidally active compositions.

The insecticide compositions are made by formulating the insecticidally active component with the desired agriculturally acceptable carrier. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally acceptable carrier" covers all adjuvants, e.g., inert components, dispersants, surfactants, tackifiers, binders, etc. that are ordinarily used in insecticide formulation technology; these are well known to those skilled in insecticide formulation.

The formulations containing the insecticidal protein and one or more solid or liquid adjuvants are prepared in known manners, e.g., by homogeneously mixing, blending and/or grinding the insecticidally active protein component with suitable adjuvants using conventional formulation techniques.

The insecticidal compositions of this invention are applied to the environment of the target lepidopteran insect, typically onto the foliage of the plant or crop to be protected, by conventional methods, preferably by spraying. Other application techniques, e.g., dusting, sprinkling, soaking, soil injection, seed coating, seedling coating or spraying, or the like, are also feasible and may be required for insects that cause root or stalk infestation. These application procedures are well known in the art.

The present invention will now be described in greater detail with reference to the following specific, illustrative examples that should not be construed as limiting the scope of the claimed invention.

EXAMPLES

Example 1

Cloning of B.t. apr Gene

An alkaline protease gene (apr) was cloned from a B.t. strain as follows.

B.t. var. kurstaki strain EG2371, a transconjugant B.t. strain that is described in U.S. Pat. No. 5,080,897 issued to González, Jr. et al. on Jan. 14, 1992, was selected since it is the active ingredient in a commercial B.t. product, Cutlass bioinsecticide (Ecogen Inc., Langhorne, Pa., the assignee of the present invention).

An oligonucleotide probe designated WD168 was synthesized having the following sequence: 5'-TGG ACA CCA AAT GAT CCA TAT TTT AAT AAT CAA TAT GG-3' (SEQ ID NO:5). This nucleotide sequence was based on an N-terminal amino acid sequence of a purified serine protease reported by Stepanov et al., *Biochem. Biophys Res. Comm.* 100:1680–1687 (1981).

Oligonucleotide probe WD168 was radioactively labeled with T4 kinase and gamma-$^{32}$P-ATP and used as a probe in Southern blot experiments carried out on total DNA from B.t. strain EG2371. The labeled probe specifically hybridized to a 12 kb EcoRI DNA fragment of B.t. strain EG2371.

A pUC18 plasmid library containing EcoRI DNA fragments of approximately 12 kb from B.t. strain EG2371 was constructed in *E. coli*. From this library, one *E. coli* colony, designated EG7299, was identified which specifically hybridized with the labeled WD168 probe.

Analysis of *E. coli* strain EG7299 showed that it contained a 14.7 kb plasmid, designated pEG1140, comprising the plasmid vector pUC18 plus a WD168-hybridizing fragment of 12 kb. A restriction map of plasmid pEG1140 is shown in FIG. 3.

Using plasmid pEG1140, a 4.3 kb XbaI-EcoRI restriction fragment was subcloned from pEG1140 onto the plasmid vector pUC18 to yield a 7.1 kb plasmid designated pEG1194. The *E. coli* strain harboring pEG1194 is designated EG7940. A restriction map of plasmid pEG1194 is shown in FIG. 4.

DNA sequencing of plasmid pEG1194 by the dideoxy method of Sanger et al., "DNA sequencing with chain-terminating inhibitors," *Proc. Natl. Acad. Sci. USA* 74:5463–5467 (1977), revealed that the 4.3 kb XbaI-EcoRI fragment contained an open reading frame that was designated as the "apr" gene. The apr gene was a wild type gene.

The nucleotide sequence of the apr gene (SEQ ID NO:1) is shown in FIG. 1. The apr gene has a coding region extending from nucleotide positions 225 to 1418 (including the TAA stop codon). The restriction site for SstI at nucleotide 954 within the apr gene is also shown in FIG. 1, and this restriction site was utilized in the next Example.

The amino acid sequence of the alkaline protease protein, designated Apr (SEQ ID NO:2), encoded by the apr gene is also shown in FIG. 1. The amino acid sequence of the Apr protein, as deduced from the DNA sequence of the apr gene, contains 397 amino acids. The molecular mass of the deduced Apr protein is 42,339 Da.

Comparisons of the Apr amino acid sequence against other polypeptides in computer databases revealed that it shows 75% identity with the thermitase proteolytic protein of *Thermoactinomyces vulgaris*, described by Meloun et al., "Complete primary structure of thermitase from *Thermoactinomyces vulgaris* and its structural features related to the subtilisin-type proteinases," *FEBS Letters* 183:195–200 (1985), and 41% identity to the subtilisin type alkaline protease protein of *B. subtilis*, described by Stahl et al., *J. Bacteriol.* 158:411–418 (1984).

The upstream portion of the apr gene, which includes the gene regulatory region, extending from nucleotide positions 1 to 615 in FIG. 1, and shown in FIG. 4, was discovered to be 99.8% identical to the exoproteinase gene promoter at nucleotide positions 485 to 1100 reported by Geiser in PCT International Patent Application Publication No. WO 92/14826 of Ciba-Geigy AG, published Sep. 3, 1992.

Example 2

In Vitro Deletion Modification of the apr Gene

A genetically disabled version of the apr gene was prepared as follows, by deletion of a portion of the DNA within the coding region of the apr gene.

Plasmid pEG1194, described in Example 1 and shown in FIG. 4, was digested with the restriction endonuclease enzyme SstI which cuts at nucleotide position 954 of the apr gene shown in FIG. 1. After the SstI digestion, approximately 2 μg of the linearized plasmid pEG1194 was treated with 2 units of Bal 31 exonuclease for approximately 3–10 minutes at 30° C. This treatment resulted in the deletion of approximately 600 nucleotides on each side of the original SstI restriction site. Bal 31 exonuclease is an enzyme that digests the ends of both DNA strands, and the size of the deletion is controlled by varying the incubation time, temperature and enzyme concentration.

The Bal 31-treated plasmid strands were then religated with T4 DNA ligase to yield a 6.2 kb plasmid pEG1203. A restriction map of plasmid pEG1203 is shown in FIG. 5. Plasmid pEG1203 is made of plasmid vector pUC18 plus a 3.1 kb XbaI-EcoRI DNA restriction fragment. The 3.1 kb fragment also contains a deleted version of the apr gene which is missing approximately 600 nucleotides on each side of the original SstI restriction site and is called herein a "disabled" gene or DNA construct. This disabled version of the apr gene is a genetically disabled apr gene that was designated as the "apr1" allele. Plasmid pEG1203 containing the apr1 allele was utilized as described in Example 3.

Example 3

In Vivo Deletion Modification of the apr Gene

A genetically disabled version of the apr gene, the apr1 allele, described in Example 2, was introduced into B.t. strain EG2371 via homologous recombination as explained below, to replace the wild-type apr gene with the apr1 allele. The following homologous recombination method is similar to that of Delecluse et al., *J. Bacteriol.* 173:3374–3381 (1991), was used. Delecluse et al. (1991) describe the disabling of the cytA in B.t. var. israelensis. Delecluse et al. (1991) deleted a portion of the cloned B.t. cytA gene in vitro and subsequently used the in vitro deleted cytA gene to displace, in vivo, the wild-type cytA gene in B.t. var. israelensis by homologous recombination.

Plasmid pEG491 contains a temperature-sensitive Bacillus vector pTV32Ts (described by Youngman et al., in "Regulation of Procaryotic Development, Smith et al., eds., *Amer. Soc. Microbiol.*, Washington, D.C., pp. 65–68 (1989), ligated into the BamHI site of the *E. coli* plasmid vector pUC18. Plasmid pEG491 is capable of replicating at 30° C. where it confers chloramphenicol resistance to B.t. cells, but it cannot replicate at 42° C.

Plasmid pEG1203 from Example 2, containing the apr1 gene, and plasmid pEG491, having temperature-sensitive replication, were digested with restriction enzymes XbaI and EcoRI. The mixture containing both digested plasmids was ligated with T4 ligase. The mixture was electroporated into B.t. strain EG10368 and chloramphenicol resistant colonies were selected at 30° C. B.t. var. kurstaki strain EG10368 is an apr$^+$, acrystalliferous (crystal negative or Cry$^-$ strain that does not produce crystal protein) B.t. strain that is readily transformable with plasmids containing various cloned B.t. toxin protein genes. B.t. strain EG10368 is described in U.S. Pat. No. 5,322,687 issued to Donovan et al. on Jun. 21, 1994.

One chloramphenicol resistant B.t. colony, designated EG7950, was studied further. Analysis of EG7950 showed that the strain contained a 10.3 kb plasmid, designated pEG1212, that contained the 3.1 kb XbaI-EcoRI restriction fragment of pEG1203 including the apr1 allele plus the 6.1 kb XbaI-EcoRI fragment of pEG491 including the temperature-sensitive replication. A restriction map of pEG1212 is shown in FIG. 6.

Plasmid pEG1212 was isolated from B.t. strain EG7950 by a standard alkaline cell lysis procedure and was then transformed into B.t. strain EG2371 by electroporation (Macaluso et al., *J. Bacteriol.* 173:1353–1356 (1991)).

B.t. strain EG2371 transformants harboring plasmid pEG1212 formed chloramphenicol resistant colonies at 30° C. Plasmid pEG1212 contains the apr1 allele and can replicate in B.t. at 30° C. conferring chloramphenicol resistance. pEG1212 cannot replicate in B.t. at 42° C. and can confer chloramphenicol resistance to B.t. at 42° C. only if the plasmid integrates, by homologous recombination, into the chromosomal site of the apr gene. Cells from one chloramphenicol resistant colony were grown at 42° C. in the presence of chloramphenicol. Culturing the cells under these conditions forced plasmid pEG1212 to insert by homologous recombination into the chromosome of the transformant B.t. strain EG2371 at the site of the wild-type apr gene.

The cells were then grown in the absence of antibiotic for several generations in order to allow plasmid pEG1212 to excise out of the chromosome and to become lost from the cultured cells. Cells that had lost plasmid pEG1212 would be sensitive to chloramphenicol.

The dynamics of homologous recombination and excision are such that, in a certain fraction of the chloramphenicol sensitive cells, the apr$^+$ gene would have been replaced by the apr1 allele. Accordingly, several chloramphenicol sensitive colonies were examined by Southern blot DNA analysis in order to identify colonies in which a 4.3 kb XbaI-EcoRI DNA restriction fragment containing the apr$^+$ gene was replaced by a 3.1 kb XbaI-EcoRI DNA fragment containing the apr1 allele.

In this procedure, total DNA was extracted from several chloramphenicol sensitive colonies and the DNA was digested with XbaI and with EcoRI. The double digested DNA was electrophoresed through an agarose gel, and the DNA was blotted onto a nitrocellulose filter. The filter was probed with plasmid pEG1194 which had been radioactively labeled. The pEG1194 probe hybridized with a 3.1 kb XbaI-EcoRI DNA fragment from one colony. That colony was designated as B.t. strain EG10587. B.t. strain EG10587 is a derivative of B.t. strain EG2371 in which the apr1 allele has replaced the apr⁺ gene and thus contains a genetically disabled, modified apr gene.

Example 4

Proteolytic Activity of B.t. Strains EG2371 (apr⁺) and EG10587 (apr1)

B.t. strain EG10587 (apr1) is genetically identical with B.t. strain EG2371 (apr⁺) with the exception that B.t. strain EG10587 contains the apr1 allele in place of the apr⁺ gene of strain EG2371, as described in Example 3. The respective proteolytic activities of cell cultures of B.t. strains EG10587 and EG2371 were evaluated using the azoalbumin assay method described by Sarath et al., in *Proteolytic Enzymes, A Practical Approach*, Beynon et al., eds., IRL Press, Oxford, U.K., p. 28, (1989).

Each B.t. strain was grown overnight at 30° C. in DSG sporulation medium. DSG sporulation medium is 0.8% (w/v) Difco nutrient broth, 0.5% (w/v) glucose, 10 mM $K_2HPO_4$, 10 mM $KH_2PO_4$, 1 mM $Ca(NO_3)_2$, 0.5 MM $MgSO_4$, 10 mM $MnCl_2$, 10 mM $FeSO_4$. Cells from each culture were pelleted by centrifugation, and the resulting supernatants were tested for proteolytic activity by the azoalbumin method. 150 µl of supernatant were added to 250 µl of 2% azoalbumin, 50 mM Tris.HCl pH 8.0 and the mixture was incubated at 37° C. for 30 minutes. 1.0 ml of 10.5% trichloroacetic acid was added, the solution was mixed thoroughly and centrifuged at 8000×g for 5 min. 0.6 ml of the supernatant was transferred to a 1 cm cuvette containing 0.7 ml of 1.0 M NaOH. The absorbance at 440 nm was determined spectrophotometrically. The numerical value of the absorbance at 440 nm represents the proteolytic activity of the supernatant.

The proteolytic activity of B.t. strain EG10587, containing the genetically disabled apr1 allele, was determined to be only about 10–20% of the activity measured for B.t. strain EG2371 (apr⁺).

The study of the following Example was conducted to determine the effect of the reduced proteolytic activity of the disabled protease gene versus the non-disabled apr gene with respect to the production of proteins by the respective strains.

Example 5

Production of B.t. Proteins by B.t Strains EG2371 (apr⁺) and EG10587 (apr1)

B.t. strains EG2371 (apr⁺) and EG10587 (apr1), described in Examples 3 and 4, each contains an identical complement of B.t. toxin genes: cryIA(a), cryIA(b), cryIA (c), and cryIIA. The cryI-type genes produce large amounts of CryI-type crystalline protein of about 130 kilodaltons (kDa) and the cryII-type gene produces large amounts of crystalline protein of about 72 kDa.

Crystal protein production was evaluated for these two B.t. strains by growing each strain for four days at a temperature of 30° C. in DSG medium, until the B.t. cells had sporulated and lysed, releasing the crystalline protein and spores.

The lysed B.t. cells, spores and protein crystals were pelleted by centrifugation, and the pellet was suspended in deionized water. The suspension was treated with sodium hydroxide (0.1 N NaOH final concentration) to solubilize the crystalline proteins, and the solubilized proteins were fractionated by SDS polyacrylamide gel electrophoresis. After staining With Coomassie blue, the protein on the gels was quantified by densitometric scanning.

This protein quantification demonstrated that on a volume basis of the culture grown, B.t. strain EG10587 (apr1) produced about 2 to about 2.4 times the amount of CryI-type crystal protein as the isogenic B.t. strain EG2371 (apr⁺) produced. This demonstrated that deletion-type disablement of the apr gene from B.t. strain EG2371 results in significantly increased yields of CryI-type crystal protein. Since apr⁺ is no longer present in EG10587, having been replaced by apr1 which cannot express protease to degrade the crystal protein, a better yield of CryI-type of proteins is achieved.

Growth of B.t. strains EG2371 (apr⁺) and EG10587 (apr1) in other culture media, such as C2 medium, also resulted in more CryI-type protein being produced by B.t. strain EG10587 (apr1), but the increase was not as large. C2 medium is described in W. Donovan et al., *Mol. Gen. Genet.* 214, pp. 365–372 (1988) and contains 1% glucose, 0.2% peptone, 0.5% NZ amine-A casein hydrolysate (Sheffield Products) 0.2% yeast extract, 15 mM $(NH_4)_2SO_4$, 23 mM $KH_2PO_4$, 27 mM $K_2HPO_4$, 1 mM $MgSO_4.7H_2O$, 600 mM $CaCl_2$, 250 mM $MnCl_2$, 17 mm $ZnSO_4.7H_2O$, 17 mM $CuSO_4.5H_2O$ and 2 mM $FeSO_4.7H_2O$.

CryIIA protein production in the two B.t. strains did not appear to be affected by the presence or absence of the apr gene in the B.t. strains, since the amount of CryIIA protein appeared approximately the same for the two B.t strains. This result indicates that the CryIIA protein is not degraded to any significant extent by alkaline protease.

Example 6

Insecticidal Activity of B.t. Proteins from B.t. Strains EG2371 (apr⁺) and EG10587 (apr1)

The CryI-type proteins in the B.t. crystal mixtures produced by isogenic B.t. strains EG2371 (apr⁺) and EG10587 (apr1), described in Example 5, were evaluated for insecticidal activity against three lepidopteran insect species.

B.t. strains EG2371 and EG10587 were grown at 30° C. in DSG medium for four days until sporulation and cell lysis occurred. The amounts of CryI-type crystal proteins in the sporulated cultures were determined by SDS-PAGE analysis, Coomassie blue staining and densitometer tracing. Cultures of EG2371 and EG10587 contained approximately equal amounts of CryIIA protein. In each culture, the amount of CryIIA protein was approximately 10% of the amount of CryI-type proteins and therefore, CryIIA does not significantly affect insect bioassay results. The sporulated cultures containing known amounts of CryI crystal proteins were diluted in 0.005% Triton® X-100 (v/v).

$PLC_{50}$ values of purified CryI-type crystal protein mixtures were determined against *Spodoptera exigua* (beet armyworm), *Trichoplusia ni* (cabbage looper) and *Plutella xylostella* (diamondback moth) using the bioassay procedures described by Donovan et al. in U.S. Pat. No. 5,322,687 issued Jun. 21, 1994, which is hereby incorporated herein by reference.

The $PLC_{50}$ dose is that amount of B.t. protein that killed half of the insects tested, i.e., the median lethal concentration.

Results of these bioassay studies, summarized in Table 2 below, showed no statistical difference in insecticidal activity for the three lepidopteran insect species tested, regardless of whether the CryI-type protein mixture was obtained from an apr⁺ B.t. strain or an apr1 B.t. strain.

TABLE 2

| | PLC$_{50}$ (ng CryI-type protein/well) | | |
|---|---|---|---|
| B. t. strain | S. exigua | T. ni | P. xylostella |
| EG2371 (apr$^+$) | 52 (43–61)* | 10 (8.9–12) | 4.8 (4.3–5.3) |
| EG10587 (apr1) | 69 (56–85) | 13 (11–15) | 4.3 (3.9–4.7) |

*range in parentheses indicates 95% confidence level.

Example 7

Construction of Crystal-negative B.t. Strain Containing the apr1 Allele

A derivative of B.t. strain EG10368, described in Example 3 above, was constructed in which the alkaline protease gene apr was genetically disabled by replacement with a modified apr gene, i.e., the apr1 allele. This was accomplished by utilizing plasmid pEG1212 (apr1), described in Example 3, which was electroporated into B.t. strain EG10368 using conventional techniques to yield chloramphenicol resistant B.t. colonies at 30° C. One chloramphenicol resistant colony was grown at a temperature of 42° C. to force the integration, by homologous recombination, of plasmid pEG1212 (apr1) into the chromosome of B.t. strain EG10368 at the site of the apr gene. This procedure was essentially the same as that described in Example 3. Subsequently, the B.t. cells were grown for several generations in the absence of antibiotic, and chloramphenicol sensitive colonies were identified.

Total DNA was isolated from several chloramphenicol sensitive colonies, and the DNA from each colony was digested with XbaI and EcoRI. The double digested DNA was electrophoresed through an agarose gel and blotted onto a nitrocellulose filter. The filter was probed with plasmid pEG1194 (apr$^+$), described in Example 1, that had been radioactively labeled.

The labeled plasmid pEG1194 (apr$^+$) hybridized to a 3.1 kb XbaI-EcoRI fragment from total DNA of one chloramphenicol sensitive B.t. colony. This colony, designated as B.t. strain EG10654, contained the apr1 allele in place of the apr$^+$ gene originally present in the parent strain B.t. strain EG10368. B.t. strain EG10654 is genetically disabled with respect to the apr gene and was used in the next Example to construct recombinant B.t. strains containing cloned B.t. toxin genes.

Example 8

Production of B.t. CryIIB Protein, CryIIIB3 Protein and CryET5 Protein in apr1 B.t. Strain Constructs Three recombinant B.t. strain constructs were prepared in which the alkaline protease gene apr had been genetically disabled and replaced with apr1, to demonstrate enhanced production of three B.t. crystal proteins, CryIIB, CryIIIB3 and CryET5, in the apr1 B.t. strains.

B.t. strain EG10654, an acrystalliferous B.t. strain described in Example 7, was employed as a host strain since it contained the apr1 allele, a genetically disabled, modified version of the apr gene. For comparison, the isogenic B.t. strain EG10368 (Cry$^-$ apr$^+$), also described in Example 7, was used as a host strain, since it contained the apr$^+$ gene.

CryIIB is a lepidopteran-toxic B.t. protein, related to CryIIA, that is made by the cryIIB B.t. toxin gene. Both the cryIIB gene and CryIIB protein are described in U.S. Pat. No. 5,073,632 issued to Donovan on Dec. 17, 1991, which is hereby incorporated by reference. CryIIIB3 is a coleopteran-toxic B.t. protein that is made by the cryIIIB3 B.t. toxin gene. The cryIIIB3 gene and CryIIIB3 protein are described in U.S. Pat. No. 5,264,364 issued to Donovan et al. on Nov. 23, 1993 (wherein the cryIIIB3 gene is referred to as the cryIIIC(b) gene), which is hereby incorporated herein by reference. CryET5 is a CryI-type lepidopteran-toxic B.t. protein that is made by the cryET5 B.t. toxin gene. The cryET5 gene and CryET5 protein are described in U.S. Pat. No. 5,322,687 issued to Donovan et al. on Jun. 21, 1994.

The cloned cryIIB gene, carried on recombinant plasmid pEG259 (described by Dankocsik et al., *Molec. Microbiol.* 4:2087–2094 (1990)), was introduced into the isogenic B.t. strains EG10654 (apr1) and EG10368 (apr$^+$) by conventional recombinant DNA techniques to yield transformant B.t. strains EG11437 (cryIIB$^+$ apr1) and EG11442 (cryIIB$^+$ apr$^+$), respectively. The cloned cryIIIB3 gene, carried on recombinant plasmid pEG272 (described by Donovan et al. in U.S. Pat. No. 5,264,364) was likewise introduced into the isogenic B.t. strains EG10654 (apr1) and EG10368 (apr$^+$) by conventional recombinant DNA techniques to yield transformant B.t. strains EG11438 (cryIIIB3$^+$ apr1) and EG11441 (cryIIIB3$^+$ apr$^+$), respectively.

The cloned cryET5 gene, carried on recombinant plasmid pEG1111 (described by Donovan et al. in U.S. Pat. No. 5,322,687) was likewise introduced into the isogenic B.t. strains EG10654 (apr1) and EG10368 (apr$^+$) to yield transformant B.t. strains EG11435 (cryET5$^+$ apr1) and EG7283 (cryET5$^+$ apr$^+$), respectively.

For evaluation of the respective B.t. crystal protein production by each of these recombinant B.t. strains, all four were grown at a temperature of 30° C. in DSG medium for 3–4 days, until sporulation of the B.t. cells had occurred and crystalline B.t. protein was produced.

Using the same procedure as described in Example 5, the quantity (weight per volume) of B.t. protein produced by each of the B.t. cultures was determined by SDS-PAGE analysis, Coomassie blue staining and densitometer measurements. The results of these analyses indicated that, in two of three cases, the apr-disabled B.t. strains, i.e., the strains containing the apr1 allele, produced significantly more B.t. protein than the B.t. strains containing the apr gene.

For the CryIIB protein producing strains, B.t. strain EG11437 (cryIIB$^+$ apr1) produced about 1.4 to about 5 times the amount of B.t. protein than B.t. strain EG11442 (cryIIB$^+$ apr$^+$) in which the apr gene had not been disabled.

For the CryET5 protein producing strains, B.t. strain EG11435 (cryET5$^+$ apr1) produced about 1.5 to about 5 times the amount of B.t. protein than B.t. strain EG7283 (cryET5$^+$ apr$^+$) in which the apr gene had not been disabled.

For the CryIIIB3 protein producing strains, B.t. strain EG11438 (cryIIIB3$^+$ apr1) produced a similar amount of CryIIIB3 protein as did B.t. strain EG11441 (cryIIIB3$^+$ apr$^w$+) in which the apr gene had not been disabled.

Example 9

Storage Stability of B.t. Proteins from apr1 B.t. Strain Constructs

The storage stability of the B.t. crystal proteins produced by the six recombinant B.t. strain constructs described in Example 8 was evaluated, over a seven-day period after being stored at a temperature of about 22° C. Sporulated cultures of the six recombinant B.t. strains, containing either the CryET5 crystal protein (B.t. strains EG11435 (cryET5+ apr1) and EG7283 (cryET5+ apr+)), the CryIIB protein (B.t. strains EG11437 (cryIIB+ apr1) and EG11442 (cryIIIB+ apr+)) or the CryIIIB3 protein (B.t. strains EG11438 (cryIIIB3+ apr1) and EG11441 (cryIIIB3+ apr+)) were analyzed at two time points, immediately after recovery of the sporulated cultures and after seven days. The amount of B.t. crystal protein in each of the samples was quantified by SDS-PAGE analysis, Coomassie blue staining and densitometer analysis.

Results of the procedures showed that the lepidopteran toxic CryET5 protein (of about 130 kDa) and the lepidopteran toxic CryIIB protein (of about 70 kDa) were equally stable, regardless of whether produced by an apr+ B.t. strain or an apr1 B.t. strain. This demonstrated that there were no adverse affects on stability of such proteins produced in greater amounts by the apr1 allele compared to the amount produced by the apr+ gene.

The coleopteran toxic CryIIIB3 protein (of about 73 kDa) produced by the apr1 B.t. strain EG11438 (cryIIIB3+ apr1) was stable over the seven-day period, but CryIIIB3 protein produced by the apr+ B.t. strain EG11441 (cryIIIB3+ apr+) was degraded to a lower molecular weight form of about 70 kDa. This result demonstrated that genetic disabling of the apr gene improved the storage stability of the full-length CryIIIB3 protein.

Example 10

Cloning of B.t. npr Gene

A neutral protease gene (npr) was cloned from the same B.t. var. kurstaki strain EG2371 used in other Examples above.

In initial unsuccessful attempts to clone a neutral protease gene in B.t. strain EG2371, oligonucleotide probes were designed based on the published sequence of the *B. subtilis* neutral protease gene, disclosed by Yang et al., *J. Bacteriol.* 160:15–21 (1984). The use of two *B. subtilis* neutral protease gene specific oligonucleotides as probes led to the cloning, subcloning and DNA sequencing of several DNA restriction fragments of B.t. strain EG2371. Although the cloned restriction fragments specifically hybridized to the oligonucleotide probes, extensive analysis of the cloned DNA fragments that hybridized to the probes failed to yield any evidence of a neutral protease gene in these cloned DNA fragments from B.t. strain EG2371.

Despite this lack of success in these initial attempts, a renewed effort was undertaken to clone a neutral protease gene isolated from B.t. strain EG2371 using different oligonucleotide probes, based on the amino acid. sequence of a neutral protease protein from *Bacillus cereus*, as reported by Sidler et al., *Biol. Chem. Hoppe-Seyler* 367:643–657 (1986).

One oligonucleotide probe designated WD205 was synthesized having the following sequence: 5'-GAA ATT GAT GTA ATT GGA CAT GAA TTA ACA CAT GCA GT-3' (SEQ ID NO:6). A second oligonucleotide probe designated WD206 was synthesized having the following sequence: 5'-ATG GTA TAT GGA GAA GGA GAT GGA GTA ACA TTT AC-3' (SEQ ID NO:7).

Oligonucleotide probes WD205 and WD206 were radioactively labeled with T4 kinase and gamma-$^{32}$P-ATP and used as probes in Southern blot experiments carried out on total DNA from B.t. strain EG2371. Both labeled probes specifically hybridized to two DNA fragments of B.t. strain EG2371: a 3.5 kb (approximate size) HindIII DNA restriction fragment and a 3.4 kb (approximate size) EcoRI DNA restriction fragment.

A pUC18 plasmid library containing HindIII DNA fragments of approximately 3–4 kb from B.t. strain EG2371 was constructed in *E. coli*. From this library, one *E. coli* colony, designated EG7971, was identified which specifically hybridized with the labeled WD206 probe.

Analysis of *E. coli* strain EG7971 showed that it contained a 6.2 kb plasmid, designated pEG1224, which consisted of the plasmid vector pUC18 plus a WD206hybridizing HindIII fragment of 3.4 kb. A restriction map of plasmid pEG1224 is shown in FIG. 7.

Dideoxy DNA sequencing of plasmid pEG1224 revealed that the 3.4 kb HindIII fragment contained a truncated open reading frame, and this was designated as npr1. As shown in FIG. 7, the npr1 open reading frame is truncated by the HindIII restriction site of plasmid pEG1224.

The effort to clone the complete npr open reading frame included the following steps. Plasmid pEG1224 was radioactively labeled for use as a probe in Southern blot experiments carried out on total DNA from B.t. strain EG2371. The labeled probe specifically hybridized to a unique PstI DNA restriction fragment of approximately 8.0 kb from the B.t. strain EG2371 total DNA.

A pUC18 plasmid library containing PStI DNA fragments of about 8 kb from B.t. strain EG2371 was constructed in *E. coli*. From this library, one *E. coli* colony, designated EG7973, was identified which specifically hybridized with the purified 3.4 kb HindIII npr1 fragment of plasmid pEG1224, whose restriction map is shown in FIG. 7.

Analysis of *E. coli*. strain EG7973 showed that it contained an 11.6 kb plasmid, designated pEG1228, which was made of the plasmid vector pUC18 plus an 8.0 kb PstI DNA restriction fragment that specifically hybridized to the 3.4 kb HindIII npr1 probe. A restriction map of plasmid pEG1228 is shown in FIG. 8.

Dideoxy DNA sequencing of plasmid pEG1228 revealed that the 8.0 kb PstI fragment contained a truncated open reading frame which was designated npr2. As shown in FIG. 8, the npr2 open reading frame is truncated by the PstI restriction site of plasmid pEG1228.

Using plasmid pEG1228, a 3.9 kb BamHI-PstI restriction fragment containing the npr2 open reading frame was subcloned from pEG1228 onto the plasmid vector pUC18 to yield a 6.6 kb plasmid designated pEG1233. A restriction map of plasmid pEG1233 is shown in FIG. 9.

The complete npr gene was finally cloned by the following procedure. The 3.9 kb BamHI-PstI npr2 fragment of plasmid pEG1233, shown in FIG. 9, was labeled for use as a probe in Southern blot experiments carried out on total DNA from B.t. strain EG2371. The labeled probe specifically hybridized to a BamHI-XbaI DNA restriction fragment of approximately 7.5 kb from B.t. strain EG2371 total DNA.

A pUC18 plasmid library containing BamHI-XbaI DNA fragments of about 7.5 kb from B.t. strain EG2371 was constructed in *E. coli*. From repeated screening of this library, one *E. coli* colony, designated EG7993, was eventually identified which specifically hybridized with the 3.9 kb BamHI-PstI npr2 fragment of plasmid pEG1233.

Analysis of *E. coli*. strain EG7993 showed that it contained a 10.2 kb plasmid, designated pEG1244, which comprises the plasmid vector pUC18 plus a 7.5 kb BamHI-XbaI DNA restriction fragment that specifically hybridized to the 3.9 kb BamHI-PstI npr2 fragment of plasmid pEG1233. A restriction map of plasmid pEG1244 is shown in FIG. 10.

DNA sequencing of portions of plasmids pEG1244 and pEG1233 confirmed that the 7.5 kb BamHI-XbaI DNA fragment of plasmid pEC1244 contained the complete open reading frame of the full-length neutral protease gene, npr. E. coli strain EG7993, containing plasmid pEG1244 whose restriction map is shown in FIG. 10, grew very slowly when cultured, and this suggested that the presence of the cloned, full-length npr gene, or its Npr protein product was toxic to E. coli.

The nucleotide sequence of the npr gene (SEQ ID NO:3) is shown in FIG. 2. The npr gene has a coding region extending from nucleotide positions 182 to 1882 (including the TAA stop codon). NdeI restriction sites within the npr gene at nucleotides 744, 750 and 1053 are also shown in FIG. 2. Use of these restriction sites is discussed in subsequent Examples.

The amino acid sequence of the neutral protease protein, designated Npr (SEQ ID NO: 4), encoded by the npr gene is also shown in FIG. 2. The amino acid sequence of the Npr protein, as deduced from the DNA sequence of the npr gene, contains 566 amino acids. The molecular mass of the deduced Npr protein is 60,982 Da.

Comparisons of the Npr amino acid sequence against other polypeptides in computer databases revealed that a portion of the Npr protein shows 98.7% identity with the 317 amino acids of the neutral protease protein of B. cereus, reported by Sidler et al. , Biol. Chem. Hoppe-Seyler 367:643–657 (1986). The Npr protein showed no amino acid sequence identity with a previously-reported B.t. protease, the protease of B.t. var. alesti described by Lovgren et al., Molec. Microbiol. 4:2137–2146 (1990) and little identity (52% in the C-terminal moiety) with the B. subtilis neutral protease protein described by Yang et al., J. Bacteriol. 160:15–21 (1984). The Npr neutral protease protein (SEQ ID NO:4) shows no amino acid sequence identity with the Apr alkaline protease protein (SEQ ID NO:2) of this invention, described in Example 1.

To obtain a full length npr gene that was not toxic to E. coli cells, the npr regulatory sequences were eliminated by use of the polymerase chain reaction (PCR). Elimination of the npr regulatory sequences was accomplished in the following manner.

Two oligonucleotides, designated WD280 and WD281, homologous to the beginning and end, respectively, of the npr coding region were synthesized. WD280 has the nucleotide sequence 5'-TTT CTA GAT GAA AAA GAA GAG TTT AGC AT-3' (SEQ ID NO:8) and, starting with the eighth nucleotide, it is homologous to the beginning of the npr DNA sequence from nucleotides 182 to 203 (FIG. 2). WD281 has the nucleotide sequence 5'-TTT CTA GAT TAG TTA ATA CCA ACA GCA CTA-3' (SEQ ID NO:9) and, starting with the ninth nucleotide, it is complementary to the end of the npr DNA sequence from nucleotides 1882 to 1861 (FIG. 2). Each oligonucleotide contains an XbaI DNA restriction site (5'-TCTAGA-3') at its 5' end. Oligonucleotides WD280 and WD281, and plasmid pEG1244 were used together in a PCR reaction using the GeneAmp PCR Reagent Kit according to the directions of the manufacturer (Perkin Elmer Cetus, Norwalk, Conn. The PCR reaction generated a DNA fragment having a size of 1.7 kb. The 1.7 kb fragment was digested with DNA restriction enzyme XbaI, and was ligated into the XbaI site of plasmid vector pUC18 yielding a 4.5 kb plasmid designated pEG1283. A restriction map of pEG1283 is shown in FIG. 13.

Plasmid pEG1283 comprises the pUC18 plasmid containing an inserted 1.7 kb XbaI DNA restriction fragment. The 1.7 kb DNA fragment contains only the coding region of the npr gene beginning at nucleotide 182 and ending at nucleotide 1882 of FIG. 2. The E. coli strain harboring pEG1283 is designated EG11466. EG11466 cells were found to grow well in LB medium containing 50 µg/ml ampicillin.

Example 11

In Vitro Deletion of the npr Gene

A genetically disabled version of the npr gene was prepared as follows, by deletion of a portion of the DNA within the coding region of npr2, the truncated npr allele described in Example 10.

Plasmid pEG1233, described in Example 10 and shown in FIG. 9, was digested with the restriction endonuclease enzyme NdeI, which cuts three times within npr2, the truncated npr gene.

The NdeI-digested plasmid pEG1233 was then religated with T4 DNA ligase, and the ligation mixture was transformed into E. coli. One ampicillin resistant E. coli transformant colony was designated as E. coli strain EG7980 and was identified as containing a 6.4 kb plasmid, designated as pEG1235, made of the pUC18 plasmid vector plus a 3.7 kb BamHI-PstI DNA restriction fragment. A restriction map of plasmid pEG1235 is shown in FIG. 11.

Plasmid pEG1235 contains a disabled version of the npr gene, actually being a disabled version of the npr2 allele, missing approximately 300 base pairs from the middle of the allele. The modified npr allele in plasmid pEG1235 was designated npr3. The deleted 300 bp segment constitutes the portion of the npr2 truncated gene fragment which was eliminated during NdeI digestion of plasmid pEG1233 (npr2) and its subsequent religation to yield plasmid pEG1235. The respective restriction maps are shown in FIGS. 9 and 11.

Example 12

In Vivo Deletion of the npr Gene

A genetically disabled version of the npr gene, the modified npr3 allele that is described in Example 11, was introduced into a B.t. strain (EG10368, described above in Example 3) via homologous recombination as described below, to replace a wild-type npr gene with the npr3 allele. The homologous recombination method employed was similar, in many respects, to that utilized in Example 3.

An integration vector was constructed as follows, to permit in vivo deletion of the npr gene in B.t. A 2.8 kb EcoRI fragment containing a chloramphenicol resistance determinant (a marker gene) from plasmid pNN101, described by Norton et al., Plasmid 13:211–214 (1985), was blunt-end ligated into the NdeI restriction site of plasmid pUC18, resulting in a 5.7 kb plasmid designated pEG1243. A restriction map of plasmid pEG1243 is shown in FIG. 12. Plasmid pEG1243 is capable of replicating in E. coli, conferring ampicillin and chloramphenicol resistance, but cannot replicate in B.t.

Using plasmid pEG1235 described in Example 10, having the restriction map shown in FIG. 11, a 3.7 kb Asp718-PstI DNA fragment was subcloned from plasmid pEG1235 into the unique Asp718-PstI site of plasmid pEG1243, resulting in a 9.4 kb plasmid designated pEG1245. A restriction map of plasmid pEG1245 is shown in FIG. 14. In FIG. 14, the open rectangular segment indicates plasmid pEG1243. Plasmid pEG1245 contains the npr3 allele and is able to replicate in E. coli, conferring ampicillin and chloramphenicol resistance, but cannot replicate in B.t. Plasmid pEC1245 can confer chloramphenicol resistance to B.t. only if it integrates, by homologous recombination, into the chromosomal site of the npr gene.

Plasmid pEG1245 was transformed by standard methods into *E. coli* strain GM2163 (Macaluso et al., 1991) yielding strain EG11447. Plasmid pEG1245 was subsequently isolated from EG11447 and the plasmid was used in the experiments described below.

Approximately 10 μg of plasmid pEG1245 was electroporated by conventional techniques into cells of B.t. var. kurstaki strain EG10368 (Cry$^-$ npr$^+$), described in Example 7. The electroporated B.t. cells were then spread into LB agar plates containing chloramphenicol and incubated for two days at a temperature of 30° C. After this time, fifty chloramphenicol resistant B.t. colonies appeared on the plates.

Southern blot analyses of DNA extracted from six chloramphenicol resistant B.t. colonies, using pEG1245 as a hybridization probe, showed that the DNA from each of the six colonies contained both the wild-type npr$^+$ gene and the modified npr3 allele. This result indicated that for each of the six B.t. colonies examined, plasmid pEG1245 had integrated into the B.t. chromosome by homologous recombination at the site of the npr$^+$ gene.

Three of these chloramphenicol resistant B.t. colonies were grown separately in LB nutrient medium at a temperature of 30° C. in the absence of chloramphenicol. After extended growth for about thirty generations, chloramphenicol-sensitive B.t. colonies were identified.

Total DNA was prepared from sixteen chloramphenicol sensitive colonies, and the DNA was analyzed by Southern blot analysis using radioactively labeled plasmid pEG1245 as a hybridization probe. The Southern blot analysis demonstrated that in four of the sixteen chloramphenicol sensitive B.t. colonies, the npr$^+$ gene had been replaced by the npr3 allele. The four strains containing the npr3 allele contained pEG1245-hybridizing DNA restriction fragments that were approximately 300 nucleotides shorter than the pEG1245-hybridizing DNA restriction fragments from the npr$^+$ strains.

One of the four colonies containing the npr3 allele was designated B.t. strain EG10624 and was utilized in subsequent Examples. B.t. strain EG10624 is a derivative of B.t. strain EG10368 in which the npr3 allele has replaced the npr$^+$ gene and thus contains a genetically disabled, modified (deleted) and truncated npr gene.

The remaining twelve chloramphenicol sensitive B.t. colonies contained the npr$^+$ gene. The npr3 allele had apparently been excised during the multiple generation culturing.

Example 13

Proteolytic Activity of B.t. Strains EG10368 (npr$^+$) and EG10624 (npr3)

B.t. strain EG10624 (npr3) is genetically identical with B.t. strain EG10368 (Cry$^-$ npr$^+$) with the exception that B.t. strain EG10624 contains the npr3 allele in place of the npr$^+$ gene of strain EG10368, as described in Example 12. The respective proteolytic activities of cell cultures of B.t. strains EG10624 and EG10368 were evaluated using the azoalbumin assay method described by Sarath et al., in *Proteolytic Enzymes, A Practical Approach*, Beynon et al., eds., IRL Press, Oxford, U.K., p. 28 (1989).

Each B.t. strain was grown overnight at 30° C. in DSG sporulation medium. Cells from each culture were pelleted by centrifugation, and the resulting supernatants were tested for proteolytic activity as described in Example 4.

The proteolytic activity of B.t. strain EG10624 (npr3) containing a genetically disabled npr gene, was determined to be only about 12–25% of the activity measured for B.t. strain EG10368 (npr$^+$), containing the wild-type npr gene.

Example 14

Production of B.t. CryET5 Protein, CryIIB Protein and CrvIIIB3 Protein in npr3 B.t. Strain Constructs Three recombinant B.t. strain constructs were prepared in which the neutral protease gene npr had been genetically disabled, to see if there would be enhanced production of three B.t. crystal proteins, CryET5, CryIIB and CryIIIB3, in the npr3 B.t. strains.

B.t. strain EG10624, an acrystalliferous B.t. strain described in Examples 12 and 13, was employed as the host strain, since it contained the npr3 allele, a genetically disabled, truncated and modified version of the npr gene. For comparison, the isogenic B.t. strain EG10368 (Cry$^-$ npr$^+$), also described in the previous two Examples, was used as a host strain, since it contained the npr$^+$ gene.

The lepidopteran-toxic CryIIB and CryET5 proteins and their respective cryIIB and cryET5 genes were the same as described previously, in connection with Example 8.

CryIIIB3 is a coleopteran-toxic B.t. protein that is made by the cryIIIB3 B.t. toxin gene as discussed above and as described in U.S. Pat. No. 5,264,364 issued to Donovan et al. on Nov. 23, 1993 (where the cryIIIB3 gene is referred to as the cryIIIC(b) gene).

The cloned cryET5 gene, carried on recombinant plasmid pEG1111 (described by Donovan et al. in U.S. Pat. No. 5,322,687) was introduced into the isogenic B.t. strains EG10624 (npr3) and EG10368 (npr$^+$) (EG10368 is both apr$^+$ and npr$^+$) by conventional recombinant DNA techniques to yield transformant B.t. strains EG7995 (cryET5$^+$ npr3) and EG7283 (cryET5$^+$ npr$^+$), respectively.

The cloned cryIIb gene, carried on recombinant plasmid pEG259 (described by Dankocsik et al., *Molec. Microbiol.* 4:2087–2094 (1990)) was likewise introduced into the isogenic B.t. strains EG10624 (npr3) and EG10368 (npr$^+$) to yield transformant B.t. strains EG7998 (cryIIB$^+$ npr3) and EG11442 (cryIIB$^+$ npr$^+$), respectively.

The cloned cryIIIB3 gene, carried on recombinant plasmid pEG272 (described by Donovan et al. in U.S. Pat. No. 5,264,364) was likewise introduced into the isogenic B.t. strains EG10624 (npr3) and EG10368 (npr$^+$) to yield transformant B.t. strains EG7994 (cryIIIB3$^+$ npr3) and EG11441 (cryIIIB3$^+$ npr$^+$), respectively.

For evaluation of the respective B.t. crystal protein production by each of these recombinant B.t. strains, all six were grown at a temperature of 30° C. in DSG sporulation medium for 3–4 days, until sporulation of the B.t. cells had occurred and crystalline B.t. protein was produced.

Using the same procedure as described in Example 5, the quantity (weight per volume) of B.t. protein produced by each of the B.t. cultures was determined by SDS-PAGE analysis, Coomassie blue staining and densitometer measurements. The results of this analysis indicated that the npr-disabled B.t. strains, i.e., containing the npr3 allele, produced much more B.t. protein than the npr-containing B.t. strains.

For the CryET5 protein producing strains, B.t. strain EG7995 (cryET5$^+$ npr3) produced about 2 to about 3 times more B.t. protein than did B.t. strain EG7283 (cryET5⁺ npr⁺) in which the npr gene had not been disabled.

For the CryIIB protein producing strains, B.t. strain EG7998 (cryIIB⁺ npr3) produced about 1.5 to about 3 times more B.t. protein than did B.t. strain EG11442 (cryIIB⁺ npr⁺) in which the npr gene had not been disabled.

For the CryIIIB3 protein producing strains, B.t. strain EG7994 (cryIIIB3⁺ npr3) produced about 1.3 to about 1.6 times more B.t. protein than did B.t. strain EG11441 (cryIIIB3⁺ npr⁺) in which the npr gene had not been disabled.

Example 15

Storage Stability of B.t. Proteins from npr3 B.t. Strain Constructs

The storage stability of the B.t. crystal proteins produced by the six recombinant B.t. strain constructs described in Example 15 was evaluated, over a seven day period after being stored at a temperature of about 22° C.

Sporulated cultures of the six recombinant B.t. strains, containing CryET5 crystal protein (B.t. strains EG7995 (cryET5⁺ npr3) and EG7283 (cryET5⁺ npr)) or CryIIB protein (B.t. strains EG7998 (cryIIB⁺ npr3) and EG11442 (cryIIB⁺ npr⁺)) or CryIIIB3 protein (B.t. strains EG7994 (cryIIIB3⁺ npr3) and EG11441 (cryIIIB3⁺ npr⁺)), were analyzed at two time points, immediately after recovery of the sporulated cultures and after seven days. The amount of B.t. crystal protein in each of the samples was quantified by SDS-PAGE analysis, Coomassie blue staining and densitometer analysis.

Results of the procedures showed that the lepidopteran-toxic CryET5 protein (of about 130 kDa) and the coleopteran-toxic CryIIIB3 protein (of about 70 kDa) were equally stable, regardless of whether produced by an npr⁺ B.t. strain or an npr3 B.t. strain.

For the lepidopteran-toxic CryIIB protein (of about 70 kDa) the situation was remarkably different. CryIIB protein produced by npr3 B.t. strain EG7998 (cryIIB⁺ npr3) was stable over the seven day period, but CryIIB protein produced by npr⁺ B.t. strain EG11442 (cryIIB⁺ npr⁺) was completely degraded during the storage at about 22° C. over the seven day period. Genetic disabling of the neutral protease gene npr thus has a highly positive impact on the storage stability of CryIIB protein produced by such npr3 B.t. strains.

Example 16

Insecticidal Activity of B.t. Protein from B.t. Strains EG7283 (npr⁺) and EG7995 (npr3)

The CryET5 protein produced respectively by isogenic B.t. strains EG7283 (npr⁺) and EG7995 (npr3), described in Example 15, was evaluated for insecticidal activity against two lepidopteran insect species.

B.t. strains EG7283 (npr⁺) and EG7995 (npr3) were grown at 30° C. in DSG medium for four days until sporulation and cell lysis occurred. The amounts of CryET5 crystal proteins in the sporulated cultures were determined by SDS-PAGE analysis, Coomassie blue staining and densitometer tracing. The sporulated cultures containing known amounts of CryET5 crystal proteins were diluted in 0.005% Triton X 100® (v/v).

$PLC_{50}$ values of the CryET5 protein contained in sporulated cultures of the two isogenic B.t. strains EG7283 (npr⁺) and EG7995 (npr3) were determined against *Ostrinia nubilalis* (European corn borer) and *Trichoplusia ni* (cabbage looper). Bioassay procedures similar to those described for Example 6 were employed.

Results of these bioassay studies, summarized in Table 3 below, showed no statistical difference in insecticidal activity for the two inspect species tested, regardless of whether the CryET5 protein was obtained from an npr⁺ B.t. strain or an npr3 B.t. strain.

TABLE 3

| | $PLC_{50}$ (ng CryET5/well) | |
|---|---|---|
| B. t. strain | O. nubilalis | T. ni |
| EG7283 (npr⁺) | 85 (66–110)* | 34 (27–43) |
| EG7995 (npr3) | 112 (81–164) | 22 (18–27) |

*Range in parentheses indicates 95% confidence level.

Example 17

Widespread Occurrence of the apr and npr Genes in B.t. Strains

The apr and npr genes were cloned from B.t. strain EG2371, a variety kurstaki strain. To determine whether the apr and npr genes were present in other varieties of B.t., the following experiment was conducted. Sixteen varieties of B.t. were selected from Ecogen Inc.'s strain collection: *kurstaki, aizawa, thuringiensis, kenya, pakistani, morrisoni, israelensis, entomocidus, tolworthi, dendrolimus, sotto, alesti, subtoxicus, toumanoffi, galleriae* and *japonensis*. Total DNA was extracted from each of the sixteen strains by standard procedures. The DNA was digested with restriction enzyme HindIII and the digested DNA was size fractionated by electrophoresis through an agarose gel. The DNA was blotted from the agarose gel to a nitrocellulose filter and the filter was incubated with the cloned apr gene that had been radioactively labeled with $^{32}P$-dATP plus Klenow. After incubation, the filter was washed and exposed to X-ray film. Analysis of the resulting autoradiogram showed that the labeled apr gene probe hybridized to a DNA restriction fragment from each of the sixteen B.t. strains. This result demonstrated that the apr gene is present in all sixteen varieties of B.t.

In a similar experiment, the radioactively labeled, cloned npr gene was incubated with a nitrocellulose filter containing digested DNA from each of the sixteen varieties of B.t. mentioned above. The filter was washed and exposed to X-ray film. Analysis of the resulting autoradiogram showed that the labeled npr gene probe hybridized to a DNA restriction fragment from each of the is sixteen B.t. strains. This result demonstrated that the npr gene is present in all sixteen varieties of B.t.

The present invention may be embodied in other specific forms without departing from the spirit or essential attributes thereof and, accordingly, reference should be made to the appended claims, rather than to the foregoing specification as indicating the scope of the invention.

We claim:

1. A method of reducing the proteolytic degradation of a *Bacillus thuringiensis* insecticidal toxic protein in a composition comprising the toxic protein, the method comprising including in the composition a *Bacillus thuringiensis* protease gene disabled from coding for protease capable of degrading the toxic protein, the protease gene before being disabled being selected from the group consisting of an alkaline protease gene and a neutral protease gene, the alkaline protease gene before being disabled having a nucleotide base sequence coding for the amino acid sequence identified in SEQ ID NO:2, and the neutral protease gene before being disabled has a nucleotide base sequence coding for the amino acid sequence identified in SEQ ID NO:4, whereby protease expressed by an organism with in the composition containing the disabled protease gene has reduced proteolytic activity against the toxic protein compared to protease encoded by a counterpart protease gene that has not been disabled, thereby resulting in reduced proteolytic activity against the toxic protein.

2. The method of claim 1 wherein the protease gene before being disabled is the alkaline protease gene.

3. The method of claim 2 wherein the disabled protease gene has the characteristics of an apr1 gene contained in *Bacillus thuringiensis* strain EG7950 deposited in NRRL with accession number NRRL B-21343.

4. The method of claim 2 wherein the insecticidal toxic protein is selected from the group consisting of CryI-type, CryII-type, CryIII-type, CryIV-type, CryV-type, CryET1, Cry ET4 and CryET5 protein, and mixtures thereof.

5. The method of claim 4 wherein the insecticidal toxic protein is a CryI-type protein.

6. The method of claim 2 further comprising expressing the toxic protein in the composition by including in the composition a gene coding for the insecticidal toxic protein, wherein the gene coding for the toxic protein is a gene selected from the group consisting of a cryI-type, cryII-type, cryIII-type, cryIV-type, cryV-type, cryET1, cryET4 and cryET5 gene, and mixtures thereof.

7. The method of claim 6 wherein the gene coding for the insecticidal toxic protein is a cryI-type gene.

8. The method of claim 2 wherein the composition includes *Bacillus thuringiensis* strain EG10654 deposited in NRRL with accession number NRRL B-21344.

9. The method of claim 1 wherein the protease gene before being disabled is the neutral protease gene.

10. The method of claim 9 wherein the disabled gene has the characteristics of an npr3 gene contained in *Escherichia coli* strain EG11447 deposited in NRRL with accession number NRRL B-21346.

11. The method of claim 9 wherein the insecticidal toxic protein is selected from the group consisting of CryI-type, CryII-type, CryIII-type, CryIV-type, CryV-type, CryET1, CryET4 and CryET5 protein, and mixtures thereof.

12. The method of claim 11 wherein the insecticidal toxic protein is a CryI-type protein.

13. The method of claim 9 further comprising expressing the toxic protein in the composition by including in the composition a gene coding for the insecticidal toxic protein, wherein the gene coding for the toxic protein is a gene selected from the group consisting of a cryI-type, cryII-type, cryIII-type, cryIV-type, cryV-type, cryET1, cryET4 and cryET5 gene, and mixtures thereof.

14. The method of claim 13 wherein the gene coding for the insecticidal toxic protein is a cryI-type gene.

15. The method of claim 9 wherein the composition includes *Bacillus thuringiensis* strain EG10624 deposited in NRRL with accession number NRRT B-21347.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 1750 base pairs
       (B) TYPE: nucleic acid
       (C) STRANDEDNESS: double
       (D) TOPOLOGY: circular (ii) MOLECULE TYPE: DNA (genomic)

(xi) SEQUENCE DESCRIPTION: SEQ ID NO:1:

```
AAAAGGAATG ACTCATACAT GATGAGCGTT CCTTTTTTCA TCCCCTCTTT TACTTAATTA        60
CTATCATTAA AAATATATTT ATATCAATAT TTACTCCTTT TTATTCCTTC AAAAGTTTTT       120
CACATAAATG TCATAAATCG TATGGTTTAA CTATATAGTT GAAAAGGAAT GCGACATTAA       180
GGTGTCACTG AAAAACTCAT CCAAGAAAAG GGAGGAAAAA TCTTTTGAAA AACAAAATCA       240
TCGTTTTCCT ATCTGTTTTG TCATTTATTA TTGGTGGTTT CTTCTTTAAC ACGAATACTT       300
CAAGCGCTGA AACATCATCT ACTGATTACG TTCCTAACCA ATTAATCGTT AAGTTCAAAC       360
AAAATGCATC TTTAAGTAAT GTGCAATCTT TTCATAAATC TGTCGGAGCT AATGTCTTAT       420
CTAAAGATGA TAAGTTAGGT TTTGAAGTCG TACAATTTTC AAAAGGTACT GTAAAAGAAA       480
AAATAAAGAG CTATAAAAAT AATCCAGATG TGGAATATGC AGAACCGAAT TATTACGTTC       540
ACGCCTTTTG GACTCCAAAC GACCCATATT TTAATAATCA ATACGGGTTA CAAAAGATTC       600
AAGCTCCACA AGCTTGGGAT AGCCAACGAA GTGATCCTGG TGTAAAAGTA GCTATTATTG       660
ATACAGGAGT TCAAGGCTCA CACCCTGATC TGGCTTCGAA AGTAATTTAC GGGCATGATT       720
ATGTTGATAA CGACAATACA TCTGATGATG GTAATGGTCA TGGTACACAT TGCGCTGGAA       780
TTACTGGAGC ACTTACGAAT AACAGCGTCG GAATTGCTGG TGTTGCCCCA CAAACTTCAA       840
TTTATGCTGT CCGCGTATTA GATAATCAAG GAAGTGGTAC TCTTGATGCT GTAGCGCAAG       900
GTATTCGAGA AGCTGCTGAT TCGGGTGCAA AAGTAATTAG TTTAAGTTTA GGAGCTCCAA       960
ATGGTGGTAC TGCATTACAA CAAGCCGTTC AATATGCATG GAATAAAGGC TCTGTTATAG      1020
TTGCAGCTGC TGGAAATGCT GGAAATACAA AAGCTAATTA CCCTGCTTAT TACAGCGAAG      1080
TAATTGCAGT TGCTTCTACA GATCAATCAG ATAGAAAATC TTCATTCTCT ACTTATGGTA      1140
GCTGGGTAGA TGTTGCAGCA CCAGGTTCAA ATATATATTC AACATATAAA GGAAGCACGT      1200
ATCAATCATT AAGTGGTACA TCTATGGCAA CACCTCATGT TGCAGGAGTC GCAGCTCTTT      1260
TAGCAAATCA AGGATATAGC AATACACAAA TCCGCCAAAT TATTGAGTCT ACTACTGATA      1320
AAATTAGTGG TACAGGTACG TACTGGAAAA ACGGTAGAGT CAATGCATAT AAGGCTGTAC      1380
AATACGCTAA GCAATTACAA GAAAATAAAG CTTCTTAAGA AAACTTTAAT CAGTCGATCT      1440
ACCATGAATG CAGAATAAAA TAGAAGGAGA GACTTCTATA ATTAAAGCCT CTCCTTCTTA      1500
CAAACTATAT TACTCTCCCT GCTTTTTAAC CATATGTAAA TACAGTACAA AATCCATCAT      1560
TGTCGATGAA TGACCAAGTT GACGAATCAT CGCTGTTATA TTTCCTCTAT GATATGTACC      1620
ATGATTTACG ACATGTTGCA CTAATTCTAA AATCGAAGTT TCTAATTTCC CTACGTATGG      1680
ATTCTCAATA ACAAATACAG CATTCACATC TTGTATTGTA ATTAAAAACT CTTTATATTG      1740
ATTTGCCATG                                                             1750
```

(2) INFORMATION FOR SEQ ID NO:2:

(i) SEQUENCE CHARACTERISTICS:
        (A) LENGTH: 397 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Lys Asn Lys Ile Ile Val Phe Leu Ser Val Leu Ser Phe Ile Ile
 1               5                  10                  15

Gly Gly Phe Phe Phe Asn Thr Asn Thr Ser Ser Ala Glu Thr Ser Ser
                20                  25                  30

Thr Asp Tyr Val Pro Asn Gln Leu Ile Val Lys Phe Lys Gln Asn Ala
            35                  40                  45

Ser Leu Ser Asn Val Gln Ser Phe His Lys Ser Val Gly Ala Asn Val
        50                  55                  60

Leu Ser Lys Asp Asp Lys Leu Gly Phe Glu Val Val Gln Phe Ser Lys
65                  70                  75                  80

Gly Thr Val Lys Glu Lys Ile Lys Ser Tyr Lys Asn Asn Pro Asp Val
                85                  90                  95

Glu Tyr Ala Glu Pro Asn Tyr Tyr Val His Ala Phe Trp Thr Pro Asn
            100                 105                 110

Asp Pro Tyr Phe Asn Asn Gln Tyr Gly Leu Gln Lys Ile Gln Ala Pro
        115                 120                 125

Gln Ala Trp Asp Ser Gln Arg Ser Asp Pro Gly Val Lys Val Ala Ile
    130                 135                 140

Ile Asp Thr Gly Val Gln Gly Ser His Pro Asp Leu Ala Ser Lys Val
145                 150                 155                 160

Ile Tyr Gly His Asp Tyr Val Asp Asn Asp Thr Ser Asp Asp Gly
                165                 170                 175

Asn Gly His Gly Thr His Cys Ala Gly Ile Thr Gly Ala Leu Thr Asn
            180                 185                 190

Asn Ser Val Gly Ile Ala Gly Val Ala Pro Gln Thr Ser Ile Tyr Ala
        195                 200                 205

Val Arg Val Leu Asp Asn Gln Gly Ser Gly Thr Leu Asp Ala Val Ala
    210                 215                 220

Gln Gly Ile Arg Glu Ala Ala Asp Ser Gly Ala Lys Val Ile Ser Leu
225                 230                 235                 240

Ser Leu Gly Ala Pro Asn Gly Gly Thr Ala Leu Gln Gln Ala Val Gln
                245                 250                 255

Tyr Ala Trp Asn Lys Gly Ser Val Ile Val Ala Ala Ala Gly Asn Ala
            260                 265                 270

Gly Asn Thr Lys Ala Asn Tyr Pro Ala Tyr Tyr Ser Glu Val Ile Ala
        275                 280                 285

Val Ala Ser Thr Asp Gln Ser Asp Arg Lys Ser Ser Phe Ser Thr Tyr
    290                 295                 300

Gly Ser Trp Val Asp Val Ala Ala Pro Gly Ser Asn Ile Tyr Ser Thr
305                 310                 315                 320

Tyr Lys Gly Ser Thr Tyr Gln Ser Leu Ser Gly Thr Ser Met Ala Thr
                325                 330                 335

Pro His Val Ala Gly Val Ala Ala Leu Leu Ala Asn Gln Gly Tyr Ser
            340                 345                 350

Asn Thr Gln Ile Arg Gln Ile Ile Glu Ser Thr Thr Asp Lys Ile Ser
```

```
                355                 360                 365
    Gly Thr Gly Thr Tyr Trp Lys Asn Gly Arg Val Asn Ala Tyr Lys Ala
        370                 375                 380

Val Gln Tyr Ala Lys Gln Leu Gln Glu Asn Lys Ala Ser
    385                 390                 395
```

(2) INFORMATION FOR SEQ ID NO:3:

(i) SEQUENCE CHARACTERISTICS:
        (A) LENGTH: 1960 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:3:

```
TAAGAAAATA TTGAAAAAAC CCCTTTCCAA TCGGAAAGGG GTTTTTTCAA TATTTGTTCC      60

TCAAAATTCT ACAAAACTTG AGAAATAAAT TAATTGAATT TTTAGTATAT TAATAGTGGA     120

AACATAATGC TAATATGAAA CTACTCTTTT TCAAAAAATT TTTTATTAGG GGGAAGGTTA     180

TATGAAAAAG AAGAGTTTAG CATTAGTGTT AGCGACAGGA ATGGCAGTTA CAACGTTTGG     240

AGGGACAGGC TCTGCGTTTG CGGATTCTAA AAATGTGCTC TCTACTAAGA AGTACAATGA     300

GACGGTGCAG TCACCTGAGT TTATTTCTGG TGATCTAACT GAAGCAACTG GCAAGAAAGC     360

AGAATCTGTT GTGTTTGATT ACTTAAACGC AGCAAAAGGT GATTACAAGC TAGGGGAAAA     420

GAGTGCACAA GATTCTTTCA AAGTGAAACA AGTGAAGAAA GATGCTGTAA CTGATTCAAC     480

AGTAGTACGT ATGCAACAAG TTTACGAAGG AGTGCCTGTA TGGGGTTCTA CTCAAGTAGC     540

TCACGTAAGT AAGGACGGTT CTTTAAAAGT ATTGTCTGGA ACAGTTGCAC CTGATTTAGA     600

CAAAAAGGAA AAGTTGAAAA ATAAAAATAA GATTGAAGGC GCAAAAGCAA TTGAAATCGC     660

GCAGCAAGAT TTAGGGGTAA CACCGAAATA TGAAGTAGAA CCAAAAGCGG ACTTATATGT     720

ATATCAAAAC GGTGAGGAAA CAACATATGC ATATGTTGTA AATCTAAAACT TCTTAGATCC     780

AAGCCCAGGA AACTACTACT ATTTCATTGA GGCAGACAGC GGTAAAGTAT TAAATAAGTT     840

TAATACAATT GATCATGTGA CGAATGATGA TAAGTCACCA GTTAAGCAAG AGGCTCCTAA     900

ACAGGATGCG AAAGCTGTTG TAAAGCCTGT AACAGGAACG AATAAAGTAG GAACTGGTAA     960

AGGCGTACTA GGAGATACGA AGTCTCTTAA TACAACGTTA TCTGGATCAT CTTACTACTT    1020

ACAAGATAAT ACACGCGGGG CAACGATTTT CACATATGAT GCGAAAAACC GTTCAACATT    1080

ACCAGGAACA TTATGGGCAG ATGCAGATAA TGTTTTCAAT GCAGCGTATG ATGCAGCAGC    1140

GGTAGATGCT CATTACTATG CGGGTATCAC GTATGATTAC TATAAGAATA CATTTAATCG    1200

TAATTCAATT AATGATGCAG GAGCGCCGTT AAAATCAACA GTTCATTACG GAAGTAATTA    1260

TAACAATGCA TTCTGGAACG GATCACAGAT GGTATACGGA GATGGTGATG GTGTAACATT    1320

TACTTCATTA TCTGGTGGAA TTGATGTAAT TGGTCACGAG TTAACGCATG CTGTTACGGA    1380

AAATAGTTCA AATCTAATTT ATCAAAATGA ATCAGGGGCT TTAAATGAAG CGATTTCTGA    1440

TATCTTTGGT ACTTAGTAG AATTCTATGA TAACCGTAAC CCGGATTGGG AGATTGGTGA    1500

AGATATTTAC ACACCTGGTA AAGCAGGAGA CGCGCTTCGC TCTATGAGTG ATCCTACGAA    1560

GTATGGTGAT CCAGACCATT ATTCTAAGCG TTACACTGGT TCAAGTGATA ACGGTGGCGT    1620

TCATACAAAC AGCGGCATTA TTAATAAACA AGCTTATTTA TTAGCAAATG GCGGTACGCA    1680

TTACGGTGTA ACTGTAAATG GTATCGGCAA AGATAAATTA GGTGCGATTT ACTACCGTGC    1740

AAATACACAG TATTTCACGC AATCTACTAC ATTTAGTCAA GCTCGTGCTG GTGCAGTACA    1800
```

```
AGCTGCAGCA GACTTATATG GTGCAAATTC TGCTGAAGTA GCAGCAGTTA AGCAATCATT    1860

TAGTGCTGTT GGTATTAACT AAGGACTTAA CGGATAGCTA TTAATAAAAT ACCTCAAAAA    1920

TAAAGAAGGA GCCTATGCTC CTTCTTTATT TTTTTCTCCA                          1960
```

(2) INFORMATION FOR SEQ ID NO:4:

(i) SEQUENCE CHARACTERISTICS:
        (A) LENGTH: 566 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Lys Lys Lys Ser Leu Ala Leu Val Leu Ala Thr Gly Met Ala Val
 1               5                  10                  15

Thr Thr Phe Gly Gly Thr Gly Ser Ala Phe Ala Asp Ser Lys Asn Val
             20                  25                  30

Leu Ser Thr Lys Lys Tyr Asn Glu Thr Val Gln Ser Pro Glu Phe Ile
         35                  40                  45

Ser Gly Asp Leu Thr Glu Ala Thr Gly Lys Lys Ala Glu Ser Val Val
 50                  55                  60

Phe Asp Tyr Leu Asn Ala Ala Lys Gly Asp Tyr Lys Leu Gly Glu Lys
 65                  70                  75                  80

Ser Ala Gln Asp Ser Phe Lys Val Lys Gln Val Lys Lys Asp Ala Val
                 85                  90                  95

Thr Asp Ser Thr Val Val Arg Met Gln Gln Val Tyr Glu Gly Val Pro
             100                 105                 110

Val Trp Gly Ser Thr Gln Val Ala His Val Ser Lys Asp Gly Ser Leu
         115                 120                 125

Lys Val Leu Ser Gly Thr Val Ala Pro Asp Leu Asp Lys Lys Glu Lys
130                 135                 140

Leu Lys Asn Lys Asn Lys Ile Glu Gly Ala Lys Ala Ile Glu Ile Ala
145                 150                 155                 160

Gln Gln Asp Leu Gly Val Thr Pro Lys Tyr Glu Val Glu Pro Lys Ala
                 165                 170                 175

Asp Leu Tyr Val Tyr Gln Asn Gly Glu Glu Thr Thr Tyr Ala Tyr Val
             180                 185                 190

Val Asn Leu Asn Phe Leu Asp Pro Ser Pro Gly Asn Tyr Tyr Tyr Phe
         195                 200                 205

Ile Glu Ala Asp Ser Gly Lys Val Leu Asn Lys Phe Asn Thr Ile Asp
210                 215                 220

His Val Thr Asn Asp Asp Lys Ser Pro Val Lys Gln Glu Ala Pro Lys
225                 230                 235                 240

Gln Asp Ala Lys Ala Val Val Lys Pro Val Thr Gly Thr Asn Lys Val
                 245                 250                 255

Gly Thr Gly Lys Gly Val Leu Gly Asp Thr Lys Ser Leu Asn Thr Thr
             260                 265                 270

Leu Ser Gly Ser Ser Tyr Tyr Leu Gln Asp Asn Thr Arg Gly Ala Thr
         275                 280                 285

Ile Phe Thr Tyr Asp Ala Lys Asn Arg Ser Thr Leu Pro Gly Thr Leu
     290                 295                 300

Trp Ala Asp Ala Asp Asn Val Phe Asn Ala Ala Tyr Asp Ala Ala Ala
305                 310                 315                 320
```

```
Val Asp Ala His Tyr Tyr Ala Gly Ile Thr Tyr Asp Tyr Tyr Lys Asn
            325                 330                 335
Thr Phe Asn Arg Asn Ser Ile Asn Asp Ala Gly Ala Pro Leu Lys Ser
            340                 345                 350
Thr Val His Tyr Gly Ser Asn Tyr Asn Asn Ala Phe Trp Asn Gly Ser
            355                 360                 365
Gln Met Val Tyr Gly Asp Gly Asp Gly Val Thr Phe Thr Ser Leu Ser
370                 375                 380
Gly Gly Ile Asp Val Ile Gly His Glu Leu Thr His Ala Val Thr Glu
385                 390                 395                 400
Asn Ser Ser Asn Leu Ile Tyr Gln Asn Glu Ser Gly Ala Leu Asn Glu
                405                 410                 415
Ala Ile Ser Asp Ile Phe Gly Thr Leu Val Glu Phe Tyr Asp Asn Arg
                420                 425                 430
Asn Pro Asp Trp Glu Ile Gly Glu Asp Ile Tyr Thr Pro Gly Lys Ala
            435                 440                 445
Gly Asp Ala Leu Arg Ser Met Ser Asp Pro Thr Lys Tyr Gly Asp Pro
450                 455                 460
Asp His Tyr Ser Lys Arg Tyr Thr Gly Ser Ser Asp Asn Gly Gly Val
465                 470                 475                 480
His Thr Asn Ser Gly Ile Ile Asn Lys Gln Ala Tyr Leu Leu Ala Asn
                485                 490                 495
Gly Gly Thr His Tyr Gly Val Thr Val Asn Gly Ile Gly Lys Asp Lys
                500                 505                 510
Leu Gly Ala Ile Tyr Tyr Arg Ala Asn Thr Gln Tyr Phe Thr Gln Ser
            515                 520                 525
Thr Thr Phe Ser Gln Ala Arg Ala Gly Ala Val Gln Ala Ala Ala Asp
            530                 535                 540
Leu Tyr Gly Ala Asn Ser Ala Glu Val Ala Ala Val Lys Gln Ser Phe
545                 550                 555                 560
Ser Ala Val Gly Ile Asn
                565
```

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:5:

TGGACACCAA ATGATCCATA TTTTAATAAT CAATATGG                    38

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:6:

GAAATTGATG TAATTGGACA TGAATTAACA CATGCAGT                    38

-continued (2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:7:

ATGGTATATG GAGAAGGAGA TGGAGTAACA TTTAC          35

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:8:

TTTCTAGATG AAAAAGAAGA GTTTAGCAT          29

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:9:

TTTCTAGATT AGTTAATACC AACAGCACTA          30